US012383500B2

(12) United States Patent
Migrino et al.

(10) Patent No.: US 12,383,500 B2
(45) Date of Patent: Aug. 12, 2025

(54) NANOLIPOSOME COMPOSITIONS AND METHODS OF USING THE SAME

(71) Applicant: United States Government as represented by the Department of Veterans Affairs, Washington, DC (US)

(72) Inventors: Raymond Q. Migrino, Phoenix, AZ (US); Seth Truran, Pheonix, AZ (US); Nina Karamanova, Laveen, AZ (US); Volkmar Weissig, Glendale, AZ (US); Jillian Madine, Liverpool (GB); Hannah Davies, Liverpool (GB)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 100 days.

(21) Appl. No.: 17/267,738

(22) PCT Filed: Aug. 9, 2019

(86) PCT No.: PCT/US2019/045964
§ 371 (c)(1),
(2) Date: Feb. 10, 2021

(87) PCT Pub. No.: WO2020/041012
PCT Pub. Date: Feb. 27, 2020

(65) Prior Publication Data
US 2021/0315821 A1  Oct. 14, 2021

Related U.S. Application Data

(60) Provisional application No. 62/717,463, filed on Aug. 10, 2018.

(51) Int. Cl.
| | | |
|---|---|---|
| *A61K 9/1272* | (2025.01) | |
| *A61K 9/08* | (2006.01) | |
| *A61K 38/17* | (2006.01) | |
| *A61K 47/24* | (2006.01) | |
| *A61K 47/26* | (2006.01) | |
| *A61K 47/28* | (2006.01) | |
| *A61K 47/68* | (2017.01) | |
| *A61K 47/69* | (2017.01) | |
| *A61P 25/28* | (2006.01) | |
| *G01N 33/58* | (2006.01) | |
| *G01N 33/68* | (2006.01) | |

(52) U.S. Cl.
CPC ............ *A61K 9/1272* (2013.01); *A61K 9/08* (2013.01); *A61K 38/1709* (2013.01); *A61K 47/24* (2013.01); *A61K 47/26* (2013.01); *A61K 47/28* (2013.01); *A61K 47/6849* (2017.08); *A61K 47/6913* (2017.08); *A61P 25/28* (2018.01); *G01N 33/586* (2013.01); *G01N 33/6893* (2013.01)

(58) Field of Classification Search
CPC .... A61K 9/1272; A61K 9/08; A61K 38/1709; A61K 47/24; A61K 47/26; A61K 47/28; A61K 47/6849; A61K 47/6913; A61K 47/6911; A61P 25/28; G01N 33/586; G01N 33/6893
See application file for complete search history.

(56) References Cited

U.S. PATENT DOCUMENTS

| | | | | |
|---|---|---|---|---|
| 4,940,694 | A | * 7/1990 | della Valle | ............. C07H 15/10 |
| | | | | 536/55.1 |
| 2014/0356418 | A1* | 12/2014 | Taylor | .................... A61K 38/08 |
| | | | | 514/21.4 |
| 2016/0158381 | A1* | 6/2016 | Migrino | ............. A61K 47/6911 |
| | | | | 514/17.7 |
| 2018/0086782 | A1 | 3/2018 | Esko et al. | |

FOREIGN PATENT DOCUMENTS

| | | |
|---|---|---|
| WO | WO-2015/009909 A1 | 1/2015 |
| WO | WO-2016/040891 A1 | 3/2016 |

OTHER PUBLICATIONS

Franco, D. A., et al Circulation, vol. 2012, 126, pp. 1-5, 2018.*
Liu D., et al Pharmaceutical Research, vol. 12, # 4, pp. 508-512, 1995.*
Franco, D. A., et al J Am Heart Association, vol. 5, pp , 2016.*
Kanazi, G.e., et al in Anesthesia-Anaglgesia, vol. 11, No. 2, pp. 475-481.*
Araujo JA, et al. Heme oxygenase-1, oxidation, inflammation, and atherosclerosis. Front Pharmacol. 2012;3:119.
Asahi M, et al. Antiactin-targeted immunoliposomes ameliorate tissue plasminogen activator-induced hemorrhage after focal embolic stroke. J Cereb Blood Flow Metab 2003;23:895-899.
Beach TG, et al. Arizona Study of Aging and Neurodegenerative Disorders and Brain and Body Donation Program. Neuropathology. 2015;35:354-89.
Bell RD, et al. Transport pathways for clearance of human Alzheimer's amyloid betapeptide and apolipoproteins E and J in the mouse central nervous system. J Cereb Blood Flow Metab 2007;27:909-918.
Bhaskar S, et al. Multifunctional Nanocarriers for diagnostics, drug delivery and targeted treatment across blood-brain barrier: perspectives on tracking and neuroimaging. Part Fibre Toxicol 2010; 7:3.
Bindokas VP, et al. Superoxide production in rat hippocampal neurons: selective imaging with hydroethidine. J Neurosci. 1996; 16:1324-36.
Boddapati SV, et al. Organelle-targeted nanocarriers: specific delivery of liposomal ceramide to mitochondria enhances its cytotoxicity in vitro and in vivo. Nano Lett 2008;8:2559-2563.
Boddapati SV, et al. Liposomes for drug delivery to mitochondria. Methods Mol Biol 2010;605:295-303.
Boddapati SV, et al. Mitochondriotropic liposomes. J Liposome Res 2005;15:49-58.

(Continued)

Primary Examiner — Celeste A Roney
(74) Attorney, Agent, or Firm — BALLARD SPAHR LLP

(57) ABSTRACT

Disclosed herein are compositions comprising nanoliposomes useful for the treatment and prevention of cerebrovascular and aging-related degenerative diseases.

3 Claims, 14 Drawing Sheets

(56) References Cited

OTHER PUBLICATIONS

Brahmachari S, et al. Induction of glial fibrillary acidic protein expression in astrocytes by nitric oxide. J Neurosci. 2006;26:4930-9.

Chao AC, et al. Hyperglycemia Increases the Production of Amyloid Beta-Peptide Leading to Decreased Endothelial Tight Junction. CNS Neurosci Ther. 2016;22:291-7.

Choi SA, et al. Are there differences in cerebral white matter lesion burdens between Parkinson's disease patients with or without dementia? Acta Neuropathol. 2010;119:147-9.

Coelho T, et al. Safety and efficacy of RNAi therapy for transthyretin amyloidosis. N Engl J Med 2013; 369:819-829.

Corraini P, et al. Long-Term Risk of Dementia Among Survivors of Ischemic or Hemorrhagic Stroke. Stroke; a journal of cerebral circulation. 2017;48:180-186.

Davies HA, et al. Oxidative Stress Alters the Morphology and Toxicity of Aortic Medial Amyloid. Biophys J2015;109:2363-2370.

Davies HA, et al. Expression and purification of the aortic amyloid polypeptide medin. Protein Expr Purif 2014; 98:32-7.

Dinkova-Kostova AT and Talalay P. NAD(P)H:quinone acceptor oxidoreductase 1 (NQO1), a multifunctional antioxidant enzyme and exceptionally versatile cytoprotector. Arch Biochem Biophys. 2010;501:116-23.

D'Souza GG, et al. DQAsome-mediated delivery of plasmid DNA toward mitochondria in living cells. J Control Release 2003;92:189-197.

Elbayoumi T and Weissig V. Implications of intracellular distribution of nanovesicles for bioimaging studies. J Biomed Nanotechnol 2009;5:620-633.

Etienne-Manneville S, et al. ICAM-1-coupled signaling pathways in astrocytes converge to cyclic AMP response element-binding protein phosphorylation and TNF-alpha secretion. J Immunol. 1999;163:668-74.

Fernando MS, O'Brien JT, Perry RH, English P, Forster G, McMeekin W, Slade JY, Golkhar A, Matthews FE, Barber R, Kalaria RN, Ince PG and Neuropathology Group of MC. Comparison of the pathology of cerebral white matter with post-mortem magnetic resonance imaging (MRI) in the elderly brain. Neuropathol Appl Neurobiol. 2004;30:385-95.

Franco DA, et al. Clusterin-nanoliposome complex attenuates human arteriole endothelial dysfunction induced by AL amyloid light chain proteins. American Heart Association 2012 Scientific Sessions. Los Angeles CA, 2012.

Franco DA, et al. Protective role of clusterin in preserving endothelial function in AL amyloidosis. Atherosclerosis 2012;225:220-223.

Franco DA, et al. Monosialoganglioside-containing nanoliposomes protect against AL amyloidosis light chain induced endothelial injury through Nrf2 defense pathway. 2016 Experimental Biology. San Diego CA, 2016.

Franco DA, et al. Monosialoganglioside-Containing Nanoliposomes Restore Endothelial Function Impaired by AL Amyloidosis Light Chain Proteins. J Am Heart Assoc. 2016;5.

Frijns CJ and Kappelle LJ. Inflammatory cell adhesion molecules in ischemic cerebrovascular disease. Stroke; a journal of cerebral circulation. 2002;33:2115-21.

Gilmore TD. Introduction to NF-kappaB: players, pathways, perspectives. Oncogene. 2006;25:6680-4.

Gobbi M, et al. Lipid-based nanoparticles with high binding affinity for amyloid-betal-42 peptide. Biomaterials 2010;31:6519-6529.

Gomez-Gaviro MV, et al. Betacellulin promotes cell proliferation in the neural stem cell niche and stimulates neurogenesis. Proceedings of the National Academy of Sciences of the United States of America. 2012;109:1317-22.

Haggqvist B, et al. Medin: an integral fragment of aortic smooth muscle cell-produced lactadherin forms the most common human amyloid. Proceedings of the National Academy of Sciences of the United States of America 1999;96:8669-8674.

Heppner FL, et al. Immune attack: the role of inflammation in Alzheimer disease. Nature reviews Neuroscience. 2015;16:358-72.

Iadecola C. The overlap between neurodegenerative and vascular factors in the pathogenesis of dementia. Acta Neuropathol. 2010;120:287-96.

Kitazume S, et al. Brain endothelial cells produce amyloid {beta} from amyloid precursor protein 770 and preferentially secrete the 0-glycosylated form. JBiol Chem. 2010;285:40097-103.

Klock G, et al. Chapter 7: Cell protective functions of secretory Clusterin (sCLU). Adv Cancer Res 2009; 104:115-138.

Kruithof EK. Regulation of plasminogen activator inhibitor type 1 gene expression by inflammatory mediators and statins. Thromb Haemost. 2008; 100:969-75.

Lakatta EG. The reality of aging viewed from the arterial wall. Artery research 2013;7:73- 80.

Larsson A, et al. Unwinding fibril formation of medin, the peptide of the most common form of human amyloid. Biochem Biophys Res Commun 2007;361:822-828.

Larsson A, et al. Lactadherin binds to elastin—a starting point for medin amyloid formation? Amyloid : the international journal of experimental and clinical investigation : the official journal of the International Society of Amyloidosis 2006; 13:78-85.

Ma JF, et al. Starvation triggers Abeta42 generation from human umbilical vascular endothelial cells. FEBS Lett. 2010;584:3101-6.

Ma Q. Role of nrf2 in oxidative stress and toxicity. Annu Rev Pharmacol Toxicol. 2013;53:401-26.

Mantovani A, et al. Cytokine regulation of endothelial cell function. FASEB journal: official publication of the Federation of American Societies for Experimental Biology. 1992;6:2591-9.

Mari D, et al. Hemostasis abnormalities in patients with vascular dementia and Alzheimer's disease. Thromb Haemost. 1996;75:216-8.

Migrino RQ, et al. Human microvascular dysfunction and apoptotic injury induced by AL amyloidosis light chain proteins. Am J Physiol Heart Circ Physiol. 2011;301:H2305-12.

Migrino RQ, et al. Human microvascular endothelial dysfunction induced by amyloidogenic medin. 2016 American College of Cardiology Scientific Sessions. Chicago, IL, 2016.

Migrino RQ, et al. Amyloidogenic medin induces endothelial dysfunction and vascular inflammation through the receptor for advanced glycation endproducts. Cardiovasc Res. 2017; 113:1389-1402.

Migrino RQ, et al. Human cerebral collateral arteriole function in subjects with normal cognition, mild cognitive impairment, and dementia. Am J Physiol Heart Circ Physiol. 2018;315:H284-H290.

Mucchiano G, et al. Senile aortic amyloid. Evidence for two distinct forms of localized deposits. The American journal of pathology 1992;140:871- 877.

Navab M, et al. Mildly oxidized LDL induces an increased apolipoprotein J/paraoxonase ratio. J Clin Invest 1997;99:2005-2019.

Neri S, et al. Calcein-acetyoxymethyl cytotoxicity assay: standardization of a method allowing additional analyses on recovered effector cells and supernatants. Clin Diagn Lab Immunol. 2001;8:1131-5.

Niedermann G, et al. Carboxyacyl derivatives of cardiolipin as four-tailed hydrophobic anchors for the covalent coupling of hydrophilic proteins to liposomes. Biochimica et biophysica acta 1991;1070:401-408.

Nuutinen T, et al. Clusterin: a forgotten player in Alzheimer's disease. Brain Res Rev 2009;61:89-104.

Olayanju A, et al. Brusatol provokes a rapid and transient inhibition of Nrf2 signaling and sensitizes mammalian cells to chemical toxicity-implications for therapeutic targeting of Nrf2. Free Radic Biol Med. 2015;78:202-12.

Pastor MT, et al. Amyloid toxicity is independent of polypeptide sequence, length and chirality. Journal of molecular biology. 2008;375:695-707.

Patel NR, et al. Mitochondria-targeted liposomes improve the apoptotic and cytotoxic action of sclareol. JLiposome Res 2009; 20:244-249.

Peng S, et al. Medin-amyloid: a recently characterized age-associated arterial amyloid form affects mainly arteries in the upper part of the body. Amyloid: the international journal of experimental and clinical investigation: the official journal of the International Society of Amyloidosis. 2005;12:96-102.

(56) References Cited

OTHER PUBLICATIONS

Peng S, et al. Role of aggregated medin in the pathogenesis of thoracic aortic aneurysm and dissection. Laboratory investigation; a journal of technical methods and pathology 2007;87:1195-1205.

Peng S, et al. Medin and medin-amyloid in ageing inflamed and non-inflamed temporal arteries. The Journal of pathology 2002;196:91-96.

Polin RS, et al. Detection of soluble E-selectin, ICAM-1, VCAM-1, and L-selectin in the cerebrospinal fluid of patients after subarachnoid hemorrhage. J Neurosurg. 1998;89:559-67.

Poon S, et al. Clusterin is an ATP-independent chaperone with very broad substrate specificity that stabilizes stressed proteins in a folding-competent state. Biochemistry 2000;39:15953-15960.

Prins ND and Scheltens P. White matter hyperintensities, cognitive impairment and dementia: an update. Nat Rev Neurol. 2015;11:157-65.

Re F, et al. Functionalization with ApoE-derived peptides enhances the interaction with brain capillary endothelial cells of nanoliposomes binding amyloid-beta peptide. J Biotechnol 2011;156:341-346.

Roman GC, et al. Vascular dementia: diagnostic criteria for research studies. Report of the NINDS-AIREN International Workshop. Neurology. 1993;43:250-60.

Rosenberg GA. Inflammation and white matter damage in vascular cognitive impairment. Stroke; a journal of cerebral circulation. 2009;40:520-3.

Rubio-Perez JM and Morillas-Ruiz JM. A review: inflammatory process in Alzheimer's disease, role of cytokines. ScientificWorldJournal. 2012;2012:756357.

Schmitz M, et al. Cytokine profiles and the role of cellular prion protein in patients with vascular dementia and vascular encephalopathy. Neurobiol Aging. 2015;36:2597-606.

Schreier H, et al. (Patho) physiologic pathways to drug targeting: artificial viral envelopes. J Mol Recognit, 1995;8:59-62.

Schrijvers EM, Koudstaal PJ, Hofman A, Breteler MM. Plasma clusterin and the risk of Alzheimer disease. JAMA 2011;305:1322-1326.

Schubert D, et al. Amyloid peptides are toxic via a common oxidative mechanism. Proceedings of the National Academy of Sciences of the United States of America. 1995;92:1989-93.

Schwochau GB, et al. Clusterin protects against oxidative stress in vitro through aggregative and nonaggregative properties. Kidney Int 1998;53:1647-1653.

Shabir O, et al. Neurovascular dysfunction in vascular dementia, Alzheimer's and atherosclerosis. BMC Neurosci. 2018;19:62.

Simpson JE, et al., Function MRCC and Ageing Neuropathology Study G. White matter lesions in an unselected cohort of the elderly: astrocytic, microglial and oligodendrocyte precursor cell responses. Neuropathol Appl Neurobiol. 2007; 33:410-9.

Swinney DC, et al. A small molecule ubiquitination inhibitor blocks NF-kappa B-dependent cytokine expression in cells and rats. JBiol Chem. 2002;277:23573-81.

Tan L, et al. Comparison of the immune response against polio peptides covalently-surface-linked to and internally-entrapped in liposomes. Asian Pac J Allergy Immunol 1991;9:25-30.

Torchilin VP, et al. Intracellular targets for DNA delivery: nuclei and mitochondria. Somat Cell Mol Genet 2002;27:49-64.

Torchilin VP, et al. TAT peptide on the surface of liposomes affords their efficient intracellular delivery even at low temperature and in the presence of metabolic inhibitors. Proceedings of the National Academy of Sciences of the United States of America 2001;98:8786-8791.

Trougakos IP, et al. Advances and challenges in basic and translational research on clusterin. Cancer Res 2009;69:403-406.

Truran S, et al. Adipose and leptomeningeal arteriole endothelial dysfunction induced by beta-amyloid peptide: a practical human model to study Alzheimer's disease vasculopathy. Journal of neuroscience methods 2014; 235:123-129.

Truran S, et al. Nanoliposomes protect against human arteriole endothelial dysfunction induced by B-amyloid peptide. J Cereb Blood Flow Metab 2015;36:405-412.

Truran, et al. Abstract 15482: Medin Amyloid Protein-induced human leptomeningeal arteriole endothelial dysfunction and pro-inflammatory signaling are reversed by monosialoganglioside nanoliposomes. Circulation. Nov. 14, 2017, vol. 136, No. Suppl 1.

Truran S, et al. Nanoliposomes restore endothelial function of human adipose arterioles exposed to AL amyloidosis light chain proteins. Experimental Biology 2012.San Diego CA, 2012.

Truran S, et al. Nanoliposomes protect against AL amyloid light chain protein-induced endothelial injury. J Liposome Res 2014;24:69-73.

Ungvari Z, et al. Oxidative stress in vascular senescence: lessons from successfully aging species. Front Biosci. 2008;13:5056-70.

Ungvari Z, et al. Mechanisms of vascular aging: new perspectives. J Gerontol A Biol Sci Med Sci. 2010;65:1028-41.

Vaughan De. PAI-1 and atherothrombosis. J Thromb Haemost. 2005;3:1879-83.

Wardlaw JM, et al. What are white matter hyperintensities made of? Relevance to vascular cognitive impairment. J Am Heart Assoc. 2015.

Weissig V. Mitochondrial-targeted drug and DNA delivery. Crit Rev Ther Drug Carrier Syst 2003;20:1-62.

Weissig V, et al. Liposomes and liposome-like vesicles for drug and DNA delivery to mitochondria. J Liposome Res 2006; 16:249-264.

Weissig V, et al. DQAsomes: a novel potential drug and gene delivery system made from Dequalinium. Pharm Res 1998;15:334-337.

Weissig V, et al. Covalent coupling of sugars to liposomes. Biochimica et biophysica acta 1989;1003:54-57.

Weissig V, et al. A method for preparation of liposomes with encapsulated peptide antigens and surface-linked sugar residues. Pharmazie 1991;46:56-57.

Weissig V, et al. A new hydrophobic anchor for the attachment of proteins to liposomal membranes. FEBS Lett 1986; 202:86-90.

Weissig V, et al. Selective DNA release from DQAsome/DNA complexes at mitochondria-like membranes. Drug Deliv 2000;7:1-5.

Weissig V and Torchilin VP. Mitochondriotropic cationic vesicles: a strategy towards mitochondrial gene therapy. Curr Pharm Biotechnol 2000;1:325-346.

Weissig V and Torchilin VP. Cationic bolasomes with delocalized charge centers as mitochondria- specific DNA delivery systems. Adv Drug Deliv Rev 2001;49:127-149.

Weissig V, et al. Accumulation of protein-loaded long-circulating micelles and liposomes in subcutaneous Lewis lung carcinoma in mice. Pharm Res 1998; 15:1552-1556.

Weissig VV, et al. Long-circulating gadolinium-loaded liposomes: potential use for magnetic resonance imaging of the blood pool. Colloids Surf B Biointerfitces 2000;18:293-299.

Yang L, et al. ICAM-1 regulates neutrophil adhesion and transcellular migration of TNF-alpha- activated vascular endothelium under flow. Blood. 2005;106:584-92.

Yerbury JJ, et al. The extracellular chaperone clusterin influences amyloid formation and toxicity by interacting with prefibrillar structures. FASEB journal: official publication of the Federation of American Societies for Experimental Biology 2007;21:2312-2322.

Yoshitake T, et al. Incidence and risk factors of vascular dementia and Alzheimer's disease in a defined elderly Japanese population: the Hisayama Study. Neurology. 1995;45:1161-8.

Zuliani G, et al. High interleukin-6 plasma levels are associated with functional impairment in older patients with vascular dementia. Int J Geriatr Psychiatry. 2007;22:305-11.

International Preliminary Report on Patentability was mailed on Feb. 16, 2021 by the International Searching Authority for International Application No. PCT/US2019/045964, filed on Aug. 9, 2019 and published as WO 2020/041012 on Feb. 27, 2020 (Applicant-Raymond Q. Migrino) (12 Pages).

International Search Report and Written Opinion were mailed on Mar. 31, 2020 by the International Searching Authority for International Application No. PCT/US2019/045964, filed on Aug. 9, 2019 and published as WO 2020/041012 on Feb. 27, 2020 (Applicant-Raymond Q. Migrino) (16 Pages).

(56) References Cited

OTHER PUBLICATIONS

Li Li, et al. Protection against Experimental Stroke by Ganglioside GM1 is Associated with the Inhibition of Autophagy. Plos One, 2016; 11(1): e0144219, pp. 1-13.

* cited by examiner

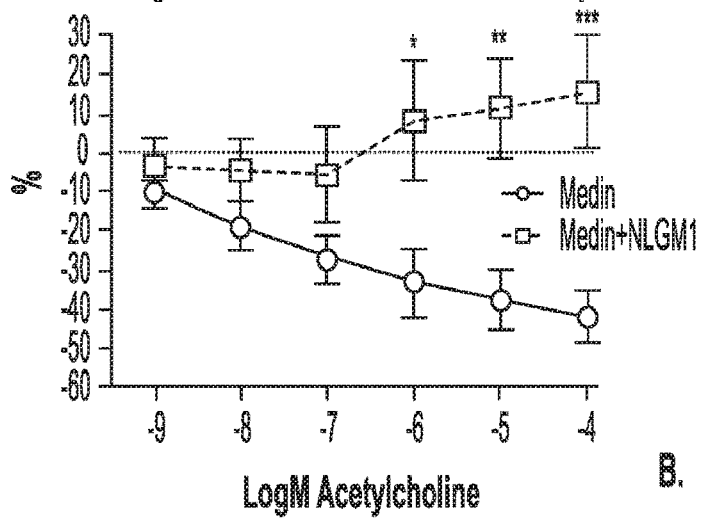
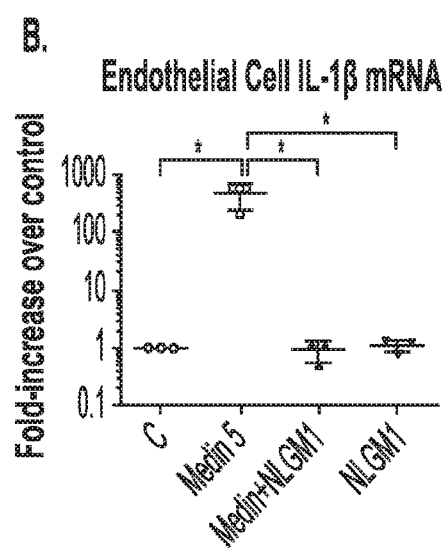
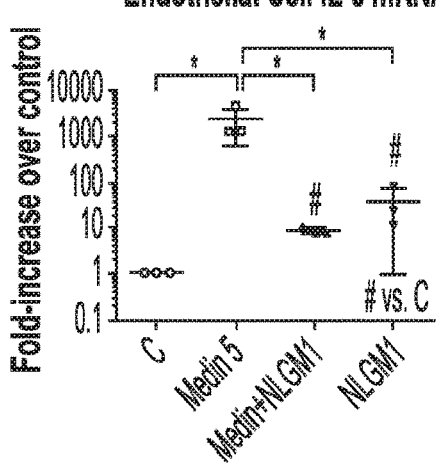
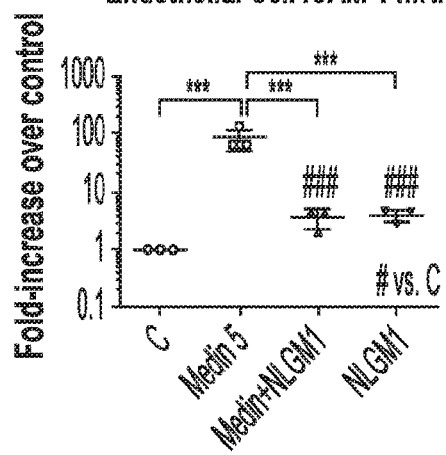
FIG. 3A
FIG. 3B
FIG. 3C
FIG. 3D

NANOLIPOSOME COMPOSITIONS AND METHODS OF USING THE SAME

CROSS REFERENCE TO RELATED APPLICATIONS

This application is a U.S. National Phase Application of International Application No. PCT/US2019/045964, filed Aug. 9, 2019, which claims the benefit of priority of U.S. Provisional Application No. 62/717,463, filed Aug. 10, 2018. The content of these earlier filed applications is hereby incorporated by reference herein in their entireties.

STATEMENT REGARDING FEDERALLY FUNDED RESEARCH

This invention was made with government support under grant numbers U24NS072026, P30AG19610, and RO1AG019795 awarded by the National Institutes of Health. The government has certain rights in the invention.

BACKGROUND

Medin is a protein that accumulates with aging, especially in the blood vessels, and causes cellular and tissue dysfunction. Some studies have shown it to be objects ≥57 years old[3-5]. It is cleaved by still unknown enzyme/s from parent protein lactadherin or milk fat globule-EGF factor 8 protein (Mfge8). Little is known about medin but it has been described as forming amyloid deposits in the media of thoracic aorta, as well as in basilar, coronary and mesenteric arteries of elderly subjects[3]. Medin co-localizes with elastic fibers of arteries[6]. Importantly, soluble medin has been implicated in aging-related vascular degenerative changes as medin immunoreactivity was found to be higher in the media of thoracic aorta aneurysms and dissections compared to control aorta; in addition, medin was shown to induce increased smooth muscle production of matrix metalloproteinase (MMP)-2, a protein that degrades elastin and collagen leading to weakening of vessel wall while promoting smooth muscle cell death[4]. Recently, it has been shown that soluble medin induces oxidative stress and reduces nitric oxide availability in endothelial cells[7]. It is now believed that medin may be a factor involved in the increased aortic stiffness that accompanies advancing age and is an important component of "vascular aging"[1, 6, 8, 9].

SUMMARY

Disclosed herein are medin-modifying nanoliposomes

Disclosed herein are medin-modifying nanoliposomes, comprising a phospholipid, cholesterol and a glycosphingolipid moiety Disclosed herein are compositions comprising a nanoliposome or a medin-modifying nanoliposome and a therapeutic cargo.

Disclosed herein are methods of treating a cerebrovascular disease, the method comprising administering to a subject with the cerebrovascular disease a therapeutically effective amount of one or more of the medin-modifying nanoliposomes, compositions or pharmaceutical compositions disclosed herein.

Disclosed herein are methods of ameliorating one or more symptoms of cerebrovascular disease, the method comprising administering to a subject with the cerebrovascular disease a therapeutically effective amount of one or more of the medin-modifying nanoliposomes, compositions or pharmaceutical compositions disclosed herein.

Disclosed herein are methods of treating or preventing aging-related degenerative disease, the method comprising administering to a subject with the aging-related degenerative disease a therapeutically effective amount of one or more of the medin-modifying nanoliposomes, compositions or pharmaceutical compositions disclosed herein.

Disclosed herein are methods of ameliorating one or more symptoms of an aging-related degenerative disease the method comprising administering to a subject with the aging-related degenerative disease a therapeutically effective amount of one or more of the medin-modifying nanoliposomes, compositions or pharmaceutical compositions disclosed herein.

Disclosed herein are methods of preventing or reversing cell or tissue toxicity of a medin protein, the method comprising administering to a subject with a cerebrovascular disease or an aging-related degenerative disease a therapeutically effective amount of one or more of the medin-modifying nanoliposomes, compositions or pharmaceutical compositions disclosed herein.

Disclosed herein are methods of preventing or reversing or reducing immune system activation, the method comprising administering to a subject with a cerebrovascular disease or an aging-related degenerative disease a therapeutically effective amount of one or more of the medin-modifying nanoliposomes, compositions or pharmaceutical compositions disclosed herein.

Disclosed herein are methods of reducing one or more proinflammatory or prothrombotic cytokines, the method comprising administering to a subject with a cerebrovascular disease or an aging-related degenerative disease a therapeutically effective amount of one or more of the medin-modifying nanoliposomes, compositions or pharmaceutical compositions disclosed herein.

Disclosed herein are methods of preventing or reversing or reducing neuroinflammation, the method comprising administering to a subject with a cerebrovascular disease or an aging-related degenerative disease a therapeutically effective amount of one or more of the medin-modifying nanoliposomes, compositions or pharmaceutical compositions disclosed herein.

Disclosed herein are methods of detecting a medin protein or a fragment thereof in a sample, the method comprising, contacting a medin-modifying nanoliposome, a nanoliposome comprising a medin binding moiety with the sample, wherein the medin-modifying nanoliposome or the nanoliposome comprising a medin binding moiety comprises a detectable label, wherein the sample comprises a detectable level of the medin protein, and detecting binding of the medin-modifying nanoliposome or the nanoliposome comprising a medin binding moiety to the medin protein.

BRIEF DESCRIPTION OF THE DRAWINGS

FIGS. 3A-D show that a medin-modifying nanoliposome (NLGM1) restored endothelial function (A) and prevented increased in IL8 (C), IL1β (B) and ICAM-1 (D) gene expression induced by medin.

FIG. 7D similarly shows that NLGM1 co-treatment restored EC viability in medin-treated cells (J-L). *p<0.05/p<0.01/*p<0.001.

FIG. 8A shows that medin induces oxidative stress (increased superoxide) in ECs treated for 20 hours which is reversed by NLGM1. The protective effect of NLGM1 is abolished by co-treatment of specific Nrf2 inhibitor brusatol. FIG. 8B shows that ECs treated with NLGM1 show increased levels of nuclear Nrf2 while co-treatment with NLGM1 and medin resulted in increased nuclear Nrf2 compared to medin treatment alone. FIGS. 8C-D show that NLGM1 co-treatment with medin increased EC protein expression of HO-1 and NQO1 but this effect was abolished in the presence brusatol. Representative Western blot images are shown in right panel. FIGS. 8E-G show that NLGM1 co-treatment restored viability in ECs treated with medin but this protection was abolished in the presence of brusatol. FIG. 8H-K shows that unlike effects on cellular viability, brusatol co-treatment did not abolish the protective effect of NLGM1 against medin-induced EC immune activation. *p<0.05, p<0.01, *p<0.001, bru-brusatol.

DETAILED DESCRIPTION

Figure 1:
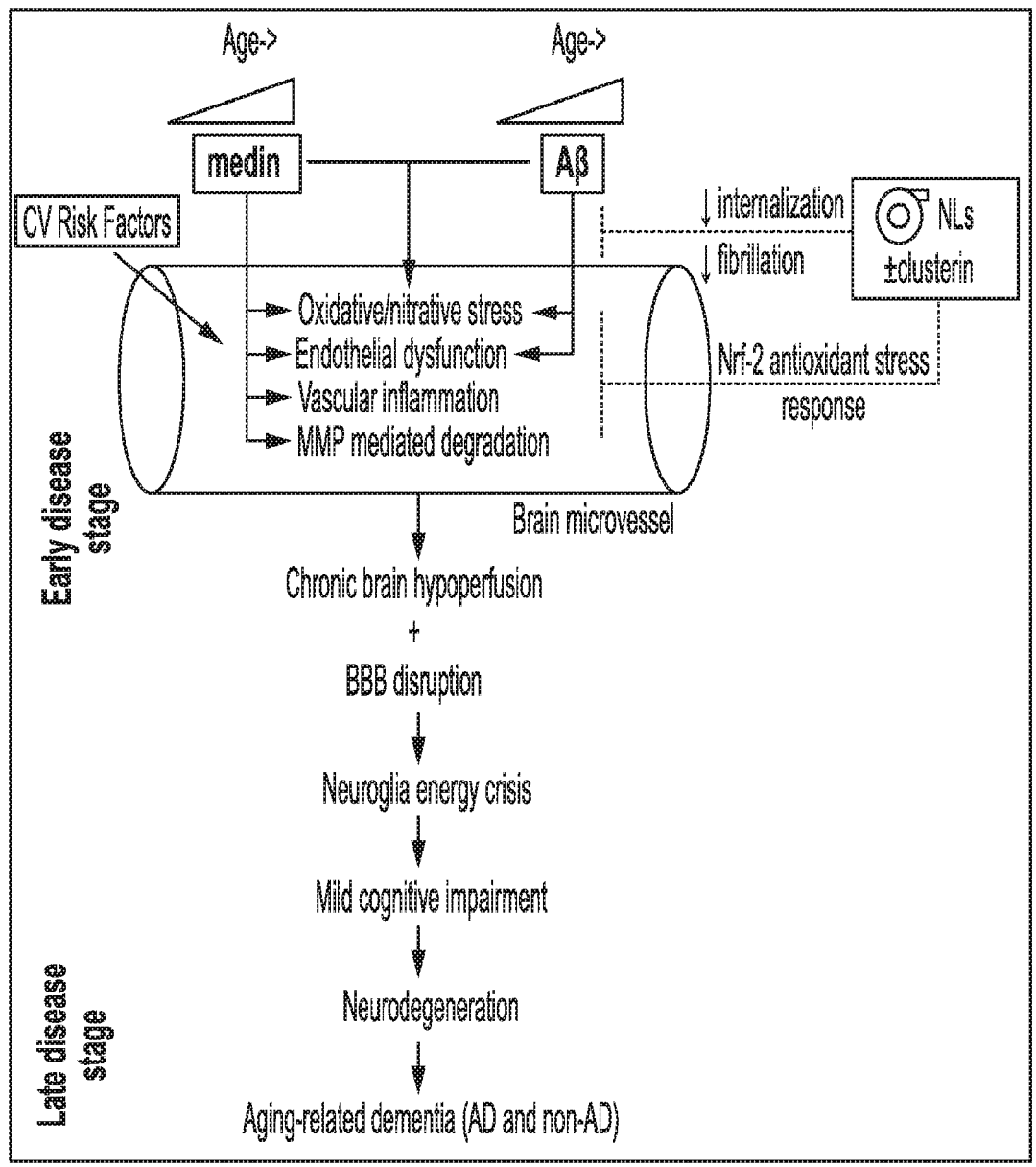
FIG. 1 shows the conceptual framework of the central role of medin and AR in cerebrovascular dysfunction leading to cognitive dysfunction with aging and testing of nanoliposome biologics to reverse the injury. Although the example shown is a blood vessel, other tissues affected by medin will also apply.

The present disclosure can be understood more readily by reference to the following detailed description of the invention, the figures and the examples included herein.

Before the present methods and gene expression panels are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment prior to the administering step.

As used herein, the term "comprising" can include the aspects "consisting of" and "consisting essentially of."

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "gene" refers to a region of DNA encoding a functional RNA or protein. "Functional RNA" refers to an RNA molecule that is not translated into a protein. Generally, the gene symbol is indicated by using italicized styling while the protein symbol is indicated by using non-italicized styling.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

By "specifically binds" is meant that an antibody recognizes and physically interacts with its cognate antigen and does not significantly recognize and interact with other antigens; such an antibody may be a polyclonal antibody or a monoclonal antibody, which are generated by techniques that are well known in the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In some aspects, preventing aging-related degenerative disease, cerebrovascular disease, cell or tissue toxicity of a medin protein, immune system activation, or neuroinflammation is intended.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a cerebrovascular disease" or "diagnosed with an aging-related degenerative disease" means having been subjected to a physical examination by a person of skill, for example, a physician, and found to have a condition that can be diagnosed or can be treated by a composition that can prevent or inhibit cell or tissue toxicity of a medin protein, immune system activation, neuroinflammation, or reduce one or more proinflammatory or prothrombotic cytokines, or a combination thereof. As a further example, "diagnosed with a need for inhibiting medin protein expression" refers to having been subjected to a physical examination by a person of skill, for example, a physician, and found to have a condition characterized by increased levels of medin or other disease wherein inhibiting medin protein expression of a population of cells would be beneficial to the subject. Such a diagnosis can be in reference to a disorder, such as a cerebrovascular disease or an aging-related degenerative disease, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a cerebrovascular disease or aging-related degenerative disease) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who performed the diagnosis.

"Inhibit," "inhibiting" and "inhibition" mean to diminish or decrease or reduce an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

As used herein, the term "biomarker" can refer to any molecular structure produced by a cell or organism having a molecular, biological or physical attribute that can be used to characterize a physiological or cellular state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multi-molecular structure or any other such structure now known or yet to be disclosed whether alone or in combination. In some aspects, the biomarker can be medin or a fragment thereof.

In some aspects, determining a level of expression of a biomarker can include quantitatively determining expression of a protein biomarker by routine methods known in the art. In some examples, an expression level of medin can be analyzed in a biological sample. Suitable biological samples include samples containing protein obtained from blood, urine or tissue from a subject, and/or protein obtained from one or more samples of control samples or subjects.

As disclosed herein, medin specific antibodies can be used for treatment of a subject or for the detection and quantification of medin expression by one of a number of immunoassay methods that are well known in the art. Methods of constructing such antibodies are known in the art. In addition, such antibodies may be commercially available. Any standard immunoassay format (such as ELISA, Western blot, or RIA assay) can be used to measure medin expression.

As used herein the term "effective amount" or "therapeutically effective amount" can refer to an amount of agent, such as a compositions comprising any of the medin-modifying nanoliposome, nanoliposomes, compositions or pharmaceutical compositions described herein, that is sufficient to generate a desired response, such as reducing or eliminating a sign or symptom of a condition or disease, such as a cerebrovascular disease or an aging-related degenerative disease characterized by overexpression of medin. Such signs or symptoms can include reduction in one or more proinflammatory or prothrombotic cytokines, preventing or reversing cell or tissue toxicity of a medin protein, preventing or reversing or reducing immune system activation, preventing, reversing or otherwise treating a cerebrovascular disease or aging-related degenerative disease, or inhibiting the expression of medin protein within a cell.

Also, as used herein, the terms "effective amount", "amount effective", and "therapeutically effective amount" can refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. For example, in some aspects, an effective amount of a disclosed medin-modifying nanoliposome, nanoliposome, composition or pharmaceutical composition is the amount effective to prevent or reduce cell or tissue toxicity of a medin protein, prevent or reverse or reduce immune system activation, reduce proinflammatory or prothrombotic cytokines, and/or inhibit medin protein expression in a desired cell or population of cells. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a disclosed composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. In some aspects, a preparation can be administered in a "prophylactically effective amount"; that is, an amount effective for prevention of a disease or condition.

As used herein, "overexpression of medin" or "increased levels of medin" refers to the production of a gene product in subject or sample that exceeds levels of production in normal, control, or non-diseased subject (e.g. a subject with cerebrovascular disease, aging-related degenerative disease, or a subject with tissue toxicity caused by a medin protein). In some aspects, "overexpression of medin" or "increased levels of medin" refers to a level of expression of medin protein in a subject sufficient to cause toxicity. Similarly, an effective amount of compositions disclosed herein can inhibit or reduce or prevent or reverse cell or tissue toxicity caused by the increased expression of medin. Methods of measuring medin protein are known in the art and can include the Western blots described herein.

"Peptide" or "polypeptide" can refer to any chain of amino acids, regardless of length or posttranslational modification (such as glycosylation, methylation, ubiquitination, phosphorylation, or the like). In some aspects, a polypeptide is a medin polypeptide. Medin is a cleave product of parent protein MFGE8 or lactadherin (gene name is MFGE8). An amino acid sequence for medin is disclosed in Davies H A, et al. Scientific Reports 2017; 7, Article number 45224.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described.

Publications cited herein and the materials for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert and applicants reserve the right to challenge the accuracy and pertinency of the cited documents. It will be clearly understood that, although a number of publications are referred to herein, such reference does not constitute an admission that any of these documents forms part of the common general knowledge in the art.

The present disclosure involves the use of nanoliposomes (which are small phospholipid particles and include but are not limited the medin-modifying nanoliposomes described herein) and anti-medin antibodies to prevent or reverse cell and tissue toxicity of the medin protein. Despite reports showing that medin is the most common and ubiquitous amyloid protein that accumulates in the vasculature with aging and reports by others that it induces toxicity to tissues (e.g., the vasculature), there is no known treatment to reverse its effects. Because medin is likely an important mediator of vascular aging, vascular inflammation and an important modulator of the interactions between age and cardiovascular risk factors leading to vascular dysfunction, the compositions and methods disclosed herein can be used for the treatment of atherosclerotic vascular disease, ischemic heart and ischemic neurologic diseases and age-related dementia disorders, diseases that comprise the major causes of mortality and morbidity in the U.S. and worldwide.

Medin is a 50 amino acid peptide that forms amyloid deposits; although it is not well-known, there is evidence that it may be the most common amyloid protein in humans[1, 2]. Disclosed herein are medin-modifying nanoliposomes and nanoliposomes which are small lipid (fat) particles that can be used to change the biologic properties of medin and that can also be used to reverse or ameliorate the deleterious effects of medin. The nanoliposomes can be formulated either as lipid particles alone, or attached to other chemicals (serving as a carrier) to reverse medin effects. Also, disclosed herein are antibodies against medin that would bind to medin, and can be used to alter medin's biologic properties and reverse or ameliorate the deleterious effects of medin.

Compositions

Disclosed herein are compositions comprising nanoliposomes. In some aspects, the nanoliposomes can be medin-modifying nanoliposomes. As used herein, the term "medin-modifying nanoliposomes" can refer to a composition that can either prevent or reverse medin's adverse effects. For example, a medin-modifying nanoliposome can reverse endothelial cell immune activation caused by medin, inhibit NFκB activation, promote Nrf2-dependent antioxidant responses, reduce or reverse increases in IL-8, IL-6, ICAM-1 or PAI-1, and restore endothelial cell viability. In some aspects, a medin-modifying nanoliposome comprises a phospholipid, cholesterol and a glycosphingolipid moiety.

The disclosed medin-modifying nanoliposomes at their core are nanoliposomes that have been modified. As such, the disclosure related to content, composition and method of making nanoliposomes can apply to the medin-modifying nanoliposomes disclosed herein. Nanoliposomes, including medin-modifying nanoliposomes, are composite structures made of phospholipids and may contain small amounts of other molecules. Though liposomes can vary in size from low micrometer range to tens of micrometers, nanoliposomes are typically in the lower size range. A nanoliposome has an aqueous solution core surrounded by a hydrophobic membrane, in the form of a lipid bilayer; hydrophilic solutes dissolved in the core cannot readily pass through the bilayer. Hydrophobic chemicals associate with the bilayer. A nanoliposome can be loaded with hydrophobic and/or hydrophilic molecules. To deliver the molecules to a site of action, the lipid bilayer can fuse with other bilayers such as the cell membrane, thus delivering the nanoliposome contents.

The choice of nanoliposome preparation method depends on the following parameters: the physicochemical characteristics of the material to be entrapped (if any) and those of the nanoliposomal ingredients; the nature of the medium in which the lipid vesicles are dispersed; the effective concentration of the entrapped substance and its potential toxicity; additional processes involved during application/delivery of the vesicles; optimum size, polydispersity and shelf-life of the vesicles for the intended application; and, batch-to-batch reproducibility and possibility of large-scale production of safe and efficient liposomal products.

In some aspects, the nanoliposomes and medin-modifying nanoliposome described herein can refer to nanoscale lipid vesicles. Nanoliposomes have the same physical, structural, thermodynamic properties manufacturing and mechanism of formation as the liposomes. In some aspects, the nanoliposomes and medin-modifying nanoliposomes disclosed herein can have a diameter <100 nm, <75 nm, <50 nm, etc.

Disclosed herein are medin-modifying nanoliposomes comprising a phospholipid, cholesterol and a glycosphingolipid moiety. In some aspects, the phospholipid can be phosphatidylcholine. In some aspects, the nanoliposomes and medin-modifying nanoliposomes can comprise phosphatidylcholine and cholesterol. Phospholipids can be used to make the nanoliposomes and medin-modifying nanoliposomes, and include but are not limited to synthetic lipids (e.g., 1,2-dipalmitoyl-sn-glycero-3-phosphocholine and ethyl-phosphatidylcholine) or natural lipids (e.g., phosphatidylcholine, sphingomyelin, and lecithin). Cholesterol can be added to the nanoliposomes and medin-modifying nanoliposomes during assembly to help maintain the stability of the membranes and reduce the permeability. The nanoliposomes and medin-modifying nanoliposomes can be functionalized. Modifications can include attachment of molecules to the exterior or encapsulation of molecules internally either in the aqueous core or lipid bilayers.

As used herein, the term "glycosphingolipid moiety" is a molecule comprising a glycosphingolipid (e.g. ceramide and oligosaccharide). Glycosphingolipids are a subtype of glycolipids containing the amino alcohol sphingosine. Glycosphingolipids can be considered as sphingolipids with an attached carbohydrate. In general, glycosphingolipids can be categorized into two groups: neutral glycosphingolipids (also called glycosphingolipids) and negatively charged glycosphingolipids. Examples of glycophingolipids include, but are not limited to cerrebrosides, gangliosides and globosides. In some aspects, the glycosphingolipid moiety can be a cerrebroside, a ganglioside, or a globoside. In some aspects, the glycosphingolipid moiety can be negatively charged.

In some aspects, the glycosphingolipid moiety can be a ganglioside. A ganglioside is a molecule composed of a glycosphingolipid with one or more sialic acids linked on the sugar chain. Gangliosides can be categorized by the number of sialic acids present, and include one NANA ("M"): GM1, GM2, and GM3; two NANAs ("D"): GD1a, GD1b, GD2, and GD3; three NANAs ("T"): GT1b and GT3; and four NANAs ("Q"): GQ1. In some aspects, the ganglioside can be GM1, GM2, GM3, GD1a, GD1b, GD2, GD3, GT1b, GT3 or GQ1. In some aspects, the ganglioside can be monosialoganglioside or GM1. In some aspects, the medin-modifying nanoliposomes can comprise phosphatidylcholine, cholesterol and GM1. Medin-modifying nanoliposomes composed of monosialoganglioside, phosphatidylcholine, and cholesterol can be referred to as GM1 ganglioside-containing nanoliposomes or monosialoganglioside-containing nanoliposomes or NLGM1. In some aspects, the molar ratio of phosphatidylcholine, cholesterol, and monosialoganglioside of the medin-modifying nanoliposome can be 70:25:5, respectively. In some aspects, the molar ratio of the phospholipid, cholesterol, and the glycosphingolipid of the medin-modifying nanoliposome can be 70:25:5, respectively. In some aspects, the molar ratio of the phospholipid or phosphatidylcholine can be 70, 80, 90 or 95 or any number in between, the cholesterol can be 25, 20, 15, 10, 5 or 0 or any number in between, and the glycosphingolipid can be about 5, 6, 7, 8, 9, or 10.

In some aspects, the nanoliposomes and medin-modifying nanoliposomes can further comprise a cargo inside of the nanopliposome or medin-modifying nanoliposome or inside the lipid bilayer. In some aspects, the nanoliposomes and medin-modifying nanoliposomes can be loaded with cargo. In some aspects, the cargo can be a molecule. In some aspects, the cargo can be therapeutic cargo. Disclosed herein are compositions comprising a nanoliposomes or medin-modifying nanoliposomes and a therapeutic cargo. In some aspects, the nanoliposomes or medin-modifying nanoliposomes can comprise a phospholipid and cholesterol. In some aspects, the phospholipid can be phosphatidylcholine. In some aspects, the therapeutic cargo can be a glycophingolipid moiety. In some aspects, the glycophingolipid moiety can be a cerrebroside, a ganglioside or a globoside. In some aspects, the therapeutic cargo can be a ganglioside. In some aspects, the ganglioside can be GM1, GM2, GM3, GD1a, GD1b, GD2, GD3, GT1b, GT3 or GQ1. In some aspects, the ganglioside can be monosialoganglioside or GM1. In some aspects, the therapeutic cargo can be clusterin. In some aspects, the therapeutic cargo can be secretory clusterin (sCLU). In some aspects, the therapeutic cargo can be apolipoprotein J. Examples of therapeutic cargoes include but not limited to apolipoproteins such as apolipoproteins A1 and E, peptides, antibodies, nucleic acids such as siRNA, aptamers, mitochondrially targeted antioxidants such as vitamin E. In some aspects, any of the compositions disclosed herein can further comprise a pharmaceutically acceptable carrier.

In some aspects, the nanoliposomes or medin-modifying nanoliposomes can comprise phosphatidylcholine, cholesterol, a ganglioside, and a therapeutic cargo. In some aspects, the therapeutic cargo can be a ganglioside. In some aspects, the ganglioside can be GM1, GM2, GM3, GD1a, GD1b, GD2, GD3, GT1b, GT3 or GQ1. In some aspects, the ganglioside can be monosialoganglioside or GM1. In some aspects, the therapeutic cargo can be clusterin. In some aspects, the therapeutic cargo can be secretory clusterin (sCLU). In some aspects, the therapeutic cargo can be apolipoprotein J. Examples of therapeutic cargoes include but not limited to apolipoproteins such as apolipoproteins A1 and E, peptides, antibodies, nucleic acids such as siRNA, aptamers, mitochondrially targeted antioxidants such as vitamin E. In some aspects, any of the compositions disclosed herein can further comprise a pharmaceutically acceptable carrier.

Disclosed herein are compositions comprising any of the nanoliposomes or medin-modifying nanoliposomes described herein. In some aspects, the compositions can further comprise a therapeutic cargo. In some aspects, the therapeutic cargo can be clusterin. In some aspects, the therapeutic cargo can be secretory clusterin (sCLU). In some aspects, the therapeutic cargo can be apolipoprotein J. Examples of therapeutic cargoes include but not limited to apolipoproteins such as apolipoproteins A1 and E, peptides, antibodies, nucleic acids such as siRNA, aptamers, mitochondrially targeted antioxidants such as vitamin E. In some aspects, any of the compositions disclosed herein can further comprise a pharmaceutically acceptable carrier. Disclosed herein are compositions comprising any of the compositions described herein. In some aspects, any of the nanoliposomes or medin-modifying nanoliposomes described herein or any of the compositions described herein can be co-formulated with one or more therapeutic agents. In some aspects, the one or more therapeutic agents can be therapeutic agents that are used to treat to a cerebrovascular disease or an aging-related degenerative disease. In some aspects, the one or more therapeutic agents that can be used to treat a cerebrovascular disease can be an antioxidant, an anti-inflammatory agent, an anti-apoptotic agent and an autophagy-modifying agent. In some aspects, the one or more therapeutic agents that can be used to treat an aging-related degenerative disease can be an antioxidant, an anti-inflammatory agent, an anti-apoptotic agent and an autophagy-modifying agent. In some aspects, the compositions can be composition can be formulated for oral, subcutaneous, intrathecal, intramuscular, inhalation, or intravenous administration.

In some aspects, any of the compositions disclosed herein can further comprise a medin binding molecule. In some aspects, the medin binding molecule comprises a medin binding moiety. In some aspects, the medin binding moiety is capable of specifically binding to medin or a fragment thereof. In some aspects, the binding moiety can be any material that can selectively form a stable complex or a covalent bond with medin or a fragment thereof. In some aspects, the binding moiety can be a peptide, antibody, small molecule, or a nucleic acid. In some aspects, the antibody can be a single chain antibody (scFv) or a Fab fragment, human, chimeric or humanized or a biologically active variant thereof, a monoclonal antibody, or a polyclonal antibody.

As used herein, the term "medin binding moiety" can be used to described a portion or a component of the medin binding molecule which binds to medin selectively and is used in herein to target the protein medin in a cell, tissue or sample from a subject (e.g. blood), for example, which is overexpressed or hyperexpressed in a cerebrovascular disease or an aging-related degenerative disease compared to normal tissue.

As noted above, any of the compositions as disclosed herein, can include an antibody or a biologically active variant thereof (e.g., an antibody the specifically binds to medin). As is well known in the art, monoclonal antibodies can be made by recombinant DNA. DNA encoding monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

In vitro methods are also suitable for preparing monovalent antibodies. As it is well known in the art, some types of antibody fragments can be produced through enzymatic treatment of a full-length antibody. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen. Antibodies incorporated into the present compositions can be generated by digestion with these enzymes or produced by other methods.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

The Fv region is a minimal fragment containing a complete antigen-recognition and binding site consisting of one heavy chain and one light chain variable domain. The three CDRs of each variable domain interact to define an antigen-biding site on the surface of the Vh-Vl dimer. Collectively, the six CDRs confer antigen-binding specificity to the antibody. As well known in the art, a "single-chain" antibody or "scFv" fragment is a single chain Fv variant formed when the VH and Vl domains of an antibody are included in a single polypeptide chain that recognizes and binds an antigen. Typically, single-chain antibodies include a polypeptide linker between the Vh and Vl domains that enables the scFv to form a desired three-dimensional structure for antigen binding.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

Methods for humanizing non-human antibodies are well known in the art. For example, humanized antibodies can be generated by substituting rodent CDRs or CDR sequences for the corresponding sequences of a human antibody. Methods that can be used to produce humanized antibodies are also well known in the art.

Pharmaceutical Compositions

As disclosed herein, are pharmaceutical compositions comprising any of the nanoliposomes or medin-modifying nanoliposomes described herein or any of the compositions described herein. In some aspects, the pharmaceutical compositions disclosed herein can further comprise an aqueous solution. In some aspects, the aqueous solution can comprise the nanoliposomes or the medin-modifying nanoliposomes. In some aspects, the aqueous solution of the pharmaceutical composition can be adjusted to a human physiological pH. In some aspects, the pharmaceutical composition can be formulated for intravenous administration. In some aspects, the pharmaceutical composition can be formulated for oral administration. In some aspects, the pharmaceutical composition can be formulated for subcutaneous, intramuscular, or intranasal administration. In some aspects, the pharmaceutical composition can be formulated for intrathecal administration. The compositions of the present disclosure also contain a therapeutically effective amount of any of the nanoliposomes or medin-modifying nanoliposomes as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the nanoliposomes or medin-modifying nanoliposomes. Thus, compositions can be prepared for parenteral administration that includes nanoliposomes or medin-modifying nanoliposomes suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. In some aspects, a dry pharmaceutical composition can be formed by drying the pharmaceutical composition. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some aspects, the disclosed pharmaceutical composition or any of the compositions disclosed herein or any of the nanoliposomes or medin-modifying nanoliposomes disclosed herein can be administered in combination with one or more therapeutic agents. In some aspects, the one or more therapeutic agents can be used to treat a cerebrovascular disease or an aging-related degenerative disease. Dosing with any of the one or more therapeutic agents (and other pharmaceutical compositions) is known in the art and can be altered to be used in combination with the disclosed pharmaceutical compositions or any of the compositions disclosed herein or any of the nanoliposomes or medin-modifying nanoliposomes disclosed herein by one of skill in the art in light of this disclosure. The one or more therapeutic agents can be given concurrently with, prior to or after the administration of any of the disclosed pharmaceutical compositions, or any of the compositions disclosed herein or any of the nanoliposomes or medin-modifying nanoliposomes disclosed herein.

Methods of Treatment

Disclosed herein are methods of treating or preventing a cerebrovascular disease. In some aspects, the methods can comprise administering to a subject with the cerebrovascular disease a therapeutically effective amount of any of the medin-modifying nanoliposomes, nanoliposomes, pharmaceutical compositions, or compositions disclosed herein. Disclosed herein are methods of ameliorating one or more symptoms of cerebrovascular disease. In some aspects, the methods can comprise administering to a subject with the cerebrovascular disease a therapeutically effective amount of any of the medin-modifying nanoliposomes, nanoliposomes, pharmaceutical compositions or compositions disclosed herein. In some aspects, the cerebrovascular disease can be cerebrovascular atherosclerosis, vascular dementia, stroke, Biswanger's disease, Alzheimer's disease, vascular cognitive impairment, cerebral amyloid angiopathy, transient ischemic attack, cerebral infarction, occlusion or stenosis of cerebral arteries, or mild cognitive impairment.

Disclosed herein methods of treating or preventing aging-related degenerative disease. IN some aspects, the methods can comprise administering to a subject with the aging-related degenerative disease a therapeutically effective amount of any of the medin-modifying nanoliposomes, nanoliposomes, pharmaceutical compositions, or compositions disclosed herein. Disclosed herein are methods of ameliorating one or more symptoms of an aging-related degenerative disease. In some aspects, the methods can comprise administering to a subject with the aging-related degenerative disease a therapeutically effective amount of any of the medin-modifying nanoliposomes, nanoliposomes, pharmaceutical compositions, or compositions disclosed herein. In some aspects, the aging-related degenerative disease can be atherosclerosis, coronary artery disease, peripheral arterial disease, peripheral vascular disease, aortic atherosclerosis, aortic aneurysm, dementia, Alzheimer's disease, mild cognitive impairment, myocardial infarction, ischemic heart disease, unstable angina, or ischemia.

Disclosed herein are methods of preventing or reversing cell or tissue toxicity of a medin protein. In some aspects, the methods can comprise administering to in a subject with a cerebrovascular disease or an aging-related degenerative disease a therapeutically effective amount of any of the nanoliposomes, medin-modifying nanoliposomes, any of the compositions or any of the pharmaceutical compositions disclosed herein.

Disclosed herein are methods of preventing or reversing or reducing immune system activation. In some aspects, the methods can comprise administering to a subject with a cerebrovascular disease or an aging-related degenerative disease a therapeutically effective amount of any of the nanoliposomes, any of the medin-modifying nanoliposomes, any of the compositions or any of the pharmaceutical compositions disclosed herein. In some aspects, the immune system activation can be associated with an increase in one or more proinflammatory or prothrombotic cytokines. In some aspects, the one or more proinflammatory cytokines can be IL-8 or IL-6. In some aspects, the one or more prothrombotic cytokines can be ICAM-1 or PAI-1.

Disclosed herein methods of reducing one or more proinflammatory or prothrombotic cytokines. In some aspects, the methods can comprise administering to a subject with a cerebrovascular disease or an aging-related degenerative disease a therapeutically effective amount of any of the nanoliposomes, any of the medin-modifying nanoliposomes, any of the compositions or any of the pharmaceutical compositions disclosed herein. In some aspects, the one or more proinflammatory cytokines can be IL-8 or IL-6. In some aspects, the one or more prothrombotic cytokines can be ICAM-1 or PAI-1.

Disclosed herein are methods of preventing or reversing or reducing neuroinflammation, the method comprising administering to in a subject with a cerebrovascular disease or an aging-related degenerative disease a therapeutically effective amount of any of the nanoliposomes, any of the medin-modifying nanoliposomes, any of the compositions or any of the pharmaceutical compositions disclosed herein.

In some aspects, the subject can be identified in need of treatment before the administration step. In some aspects, the subject can be identified as having an increased level of medin protein compared to a control subject or control sample. In some aspects, the subject can be a human. In some aspects, the increased levels of medin can be higher in the subject with the cerebrovascular disease or the aging-related degenerative disease compared to a cognitively normal or control subject or sample.

The pharmaceutical compositions described above can be formulated to include a therapeutically effective amount of any of the medin-modifying nanoliposomes or any of the nanoliposomes disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a cerebrovascular disease or an aging-related degenerative disease.

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with a cerebrovascular disease or an aging-related degenerative disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cerebrovascular disease or the aging-related degenerative disease is delayed, hindered, or prevented, or the cerebrovascular disease or an aging-related degenerative disease or a symptom of the cerebrovascular disease or an aging-related degenerative disease is ameliorated. One or more of the symptoms can be less severe. Recovery can be accelerated in an individual who has been treated.

Disclosed herein, are methods of treating a patient with a cerebrovascular disease or an aging-related degenerative disease. In some aspects, the patient can have one or more cerebrovascular disease or one or more aging-related degenerative disease or a combination thereof. In some aspects, the patient can be at risk of one or more cerebrovascular disease or one or more aging-related degenerative disease or a combination thereof. In some aspects, the patient can have one or more cerebrovascular disease or one or more aging-related degenerative disease or a combination thereof and be at risk of one or more cerebrovascular disease or one or more aging-related degenerative disease or a combination thereof.

Amounts effective for this use can depend on the severity of the cerebrovascular disease or aging-related degenerative disease and the weight and general state and health of the subject, but generally range from about 0.05 µg to about 1000 µg (e.g., 0.5-1000 µg) of an equivalent amount of the nanoliposome or medin-modifying nanoliposome per dose per subject. Suitable regimes for initial administration and booster administrations are typified by an initial administration followed by repeated doses at one or more hourly, daily, weekly, or monthly intervals by a subsequent administration. For example, a subject can receive any of the pharmaceutical compositions, compositions, nanoliposomes or medin-modifying nanoliposomes one or more times per week (e.g., 2, 3, 4, 5, 6, or 7 or more times per week). For example, a subject may receive 0.1 to 2,500 µg (e.g., 2,000, 1,500, 1,000, 500, 100, 10, 1, 0.5, or 0.1 µg) dose per week. A subject can also receive a nanoliposomes or medin-modifying nanoliposomes in the range of 0.1 to 3,000 µg per dose once every two or three weeks. A subject can also receive 2 mg/kg every week (with the weight calculated based on the weight of the nanoliposomes or medin-modifying nanoliposomes).

The total effective amount of a nanoliposomes or medin-modifying nanoliposomes in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of one or more of the therapeutic agents present within the compositions described herein and used in the methods as disclosed herein applied to mammals (e.g., humans) can be determined by one of ordinary skill in the art with consideration of individual differences in age, weight, and other general conditions (as mentioned above).

Also disclosed herein are methods of detecting a medin protein or a fragment thereof in a sample. In some aspects, the methods can comprise contacting a medin-modifying nanoliposome as described herein or a nanoliposome as described herein comprising a medin binding moiety with the sample. In some aspects, the medin-modifying nanoliposome or the nanoliposome comprising a medin binding moiety can comprise a detectable label. In some aspects, the sample can comprise a detectable level of the medin protein. In some aspects, the methods can comprise detecting binding of the medin-modifying nanoliposome or the nanoliposome comprising a medin binding moiety to the medin protein.

In some aspects, the detectable label can be any detectable moiety. For example, the detectable label can be fluorescein, HA tag, Gst-tag, EGFP-tag, FLAG™ tag or biotin.

Epitope tags are short stretches of amino acids to which a specific antibody can be raised, which in some aspects allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western blotting"), and affinity chromatography. Epitope tags add a known epitope (e.g., antibody binding site) on the subject protein, to provide binding of a known and often high-affinity antibody, and thereby allowing one to specifically identify and track the tagged protein that has been added to a living organism or to cultured cells. Examples of epitope tags include, but are not limited to, myc, T7, GST, GFP, HA (hemagglutinin), V5 and FLAG tags. The first four examples are epitopes derived from existing molecules. In contrast, FLAG is a synthetic epitope tag designed for high antigenicity (see, e.g., U.S. Pat. Nos. 4,703,004 and 4,851,341). Epitope tags can have one or more additional functions, beyond recognition by an antibody. The sequences of these tags are described in the literature and well known to the person of skill in art.

In some aspects, the disclosed methods and compositions comprise an epitope-tag wherein the epitope-tag has a length of between 6 to 15 amino acids. In an alternative aspect, the epitope-tag has a length of 9 to 11 amino acids.

As described herein, the term "immunologically binding" is a non-covalent form of attachment between an epitope of an antigen (e.g., the epitope-tag) and the antigen-specific part of an antibody or fragment thereof. Antibodies are preferably monoclonal and must be specific for the respective epitope tag(s) as used. Antibodies include murine, human and humanized antibodies. Antibody fragments are known to the person of skill and include, amongst others, single chain Fv antibody fragments (scFv fragments) and Fab-fragments. The antibodies can be produced by regular hybridoma and/or other recombinant techniques. Many antibodies are commercially available.

In some aspects, the methods can further comprise measuring (e.g., quantifying) the amount of the detected medin protein in the sample. In some aspects, the methods can further comprise comparing the amount of the detected medin protein in the sample with a control sample. In some aspects, the sample can be blood, urine or tissue. In some aspects, the amount of the detected medin protein in the sample can be higher than the amount of the medin protein in the control sample indicating an increased risk for developing or having a cerebrovascular disease or an aging-related degenerative disease. In some aspects, the amount of the detected medin protein in the sample can be lower than or about equal to the amount of the medin protein in the control sample indicating a reduced risk for developing or having a cerebrovascular disease or an aging-related degenerative disease.

EXAMPLES

Example 1: Nanoliposome and Antibody Treatment of Medin Pathology

Consistent with reports that medin was present in basilar arteries[3], it was also found that medin was present in the brain microvessel walls in 8 elderly donor brains (6 AD and 2 cognitively normal, CN) (FIG. 9). Area of medin signal comprised 42.9±9% of vessel wall area in AD and 29.5±3% in CN subjects (p=NS). The data illustrates the co-localization of Aβ42 and medin in the wall of an arteriole from an AD patient, suggesting that the amyloid fibril deposit in this subject (shown with thioflavin-S) may be composed of Aβ42 and medin. Further, the data show a small artery from middle frontal gyrus of AD patient with cerebral amyloid angiopathy. More specifically the data demonstrate diffuse amyloid fibril deposition in the arterial wall (thioflavin-S fluorescence); the presence of Aβ42; and co-localization of medin in the same arterioles (using human anti-Aβ42 and anti-medin).

Similar to Aβ, human arterioles (adipose tissue) developed endothelial dysfunction when exposed for 1 hour to medin[10]. For example, data show that medin alone causes increased endothelial cell priming and proinflammatory stimulation; the effects are synergistic when co-treated with saturated fatty acid palmitic acid (a saturated fatty acid that is a known cardiovascular risk factor). The data also show that medin treatment induced endothelial and more modest smooth-muscle dysfunction in human arterioles. This was associated with reduced endothelial cell (EC) NO and increased peroxynitrite production. Medin induced increased EC IL-8 production and upregulation of MMP-9.[10,6] This was associated with increased endothelial cell oxidative and nitrative stress, similar to Aβ42. However, unlike Aβ42, medin induced profound pro-inflammatory response and increased MMP-9 expression. These data suggest that medin induces endothelial dysfunction as well as promotes vascular inflammation and induction of signaling for matrix degradation.

Figure 2:
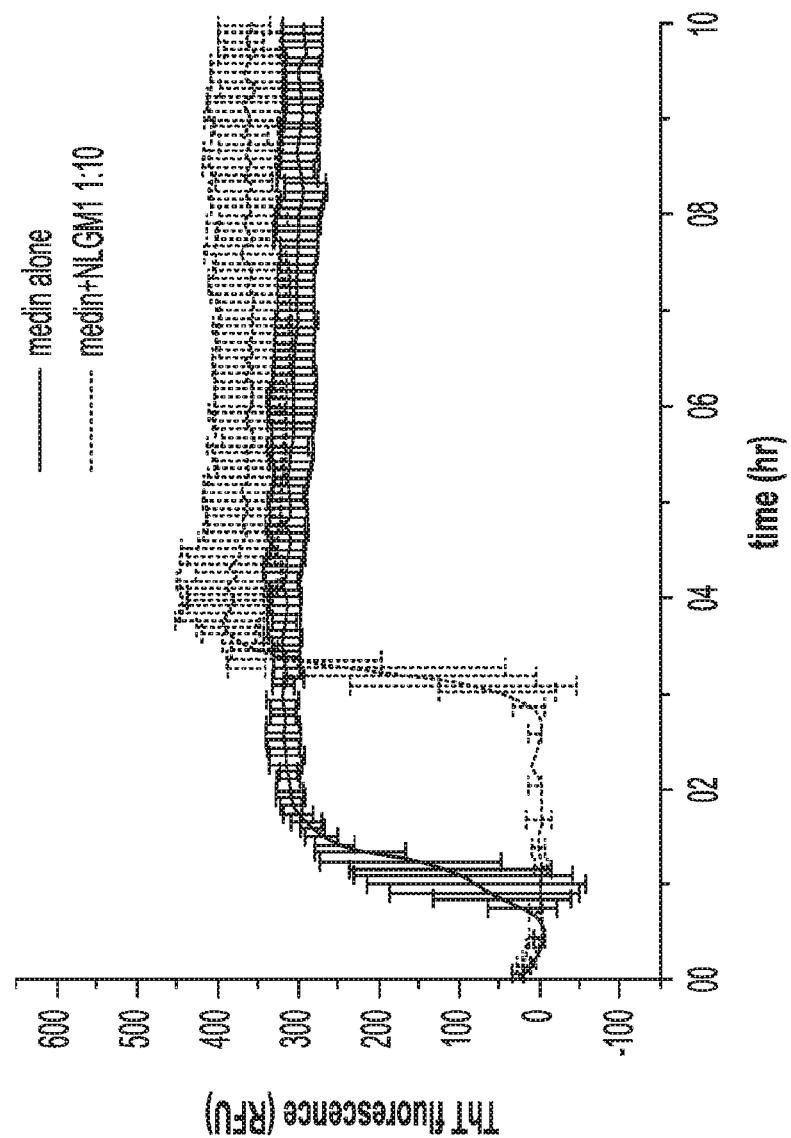
FIG. 2 shows a medin-modifying nanoliposome (monosialoganglioside containing nanoliposomes (NLGM1)) retarded the time needed for aggregation of medin.
Figure 4:
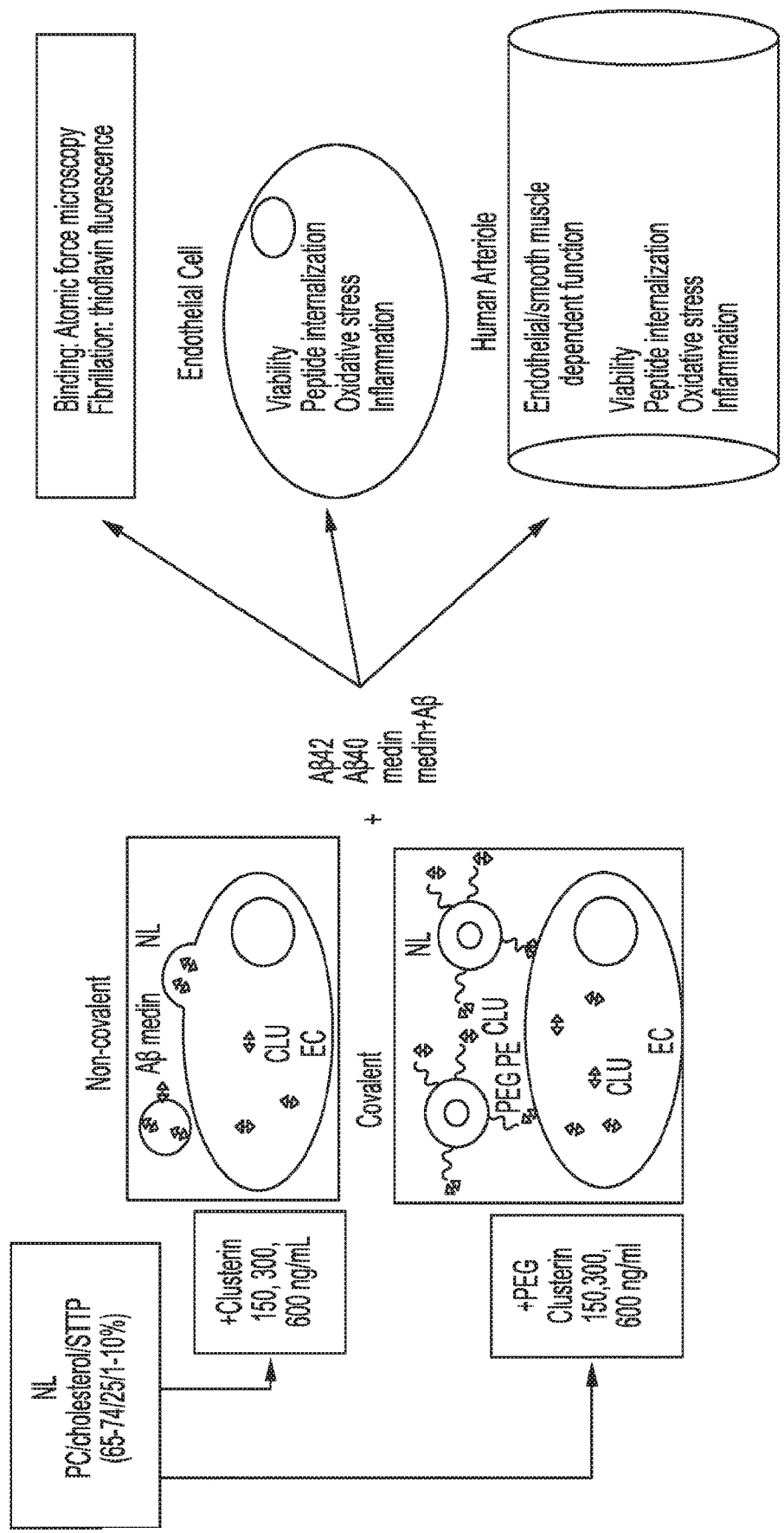
FIG. 4 shows an illustration of the possible formulations of nanoliposomes naked or conjugated with cargo (e.g., clusterin) to reverse effects of medin.
Figure 5A:
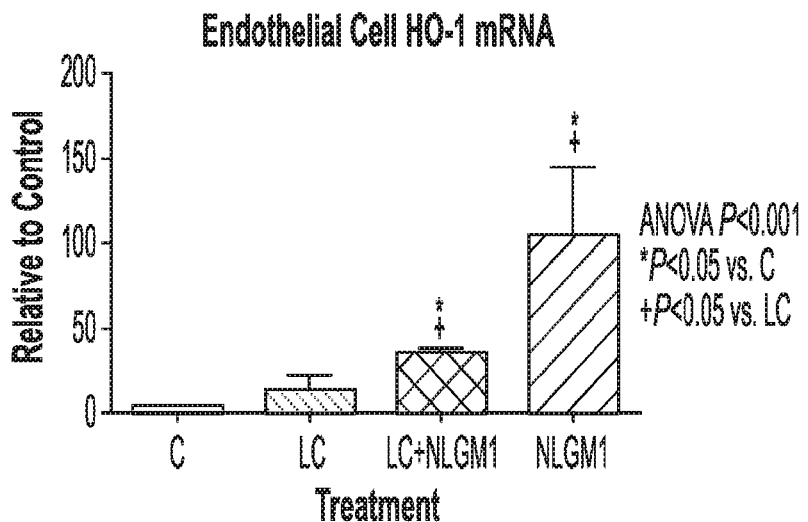
FIGS. 5A-D show that nanoliposomes, including NLGM1, induced increased gene and protein expression of antioxidant proteins when endothelial cells (HO-1 mRNA (A); HO-1 protein (B); NQO1 mRNA (C); and NQO1 protein (D) are exposed to amyloid LC protein and nanoliposomes. The antioxidant stress response is mediated via Nrf-2 activation.
Figure 5B:
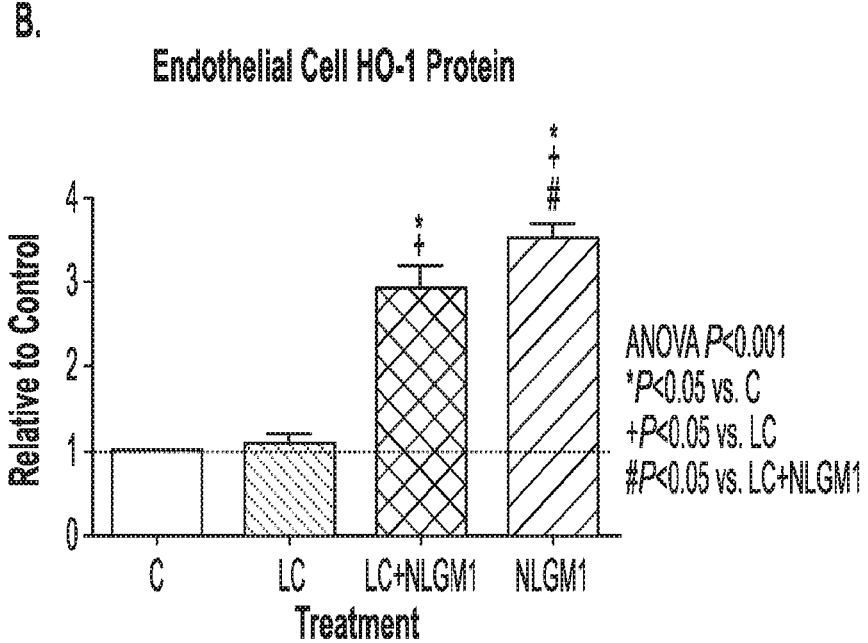
Figure 5C:
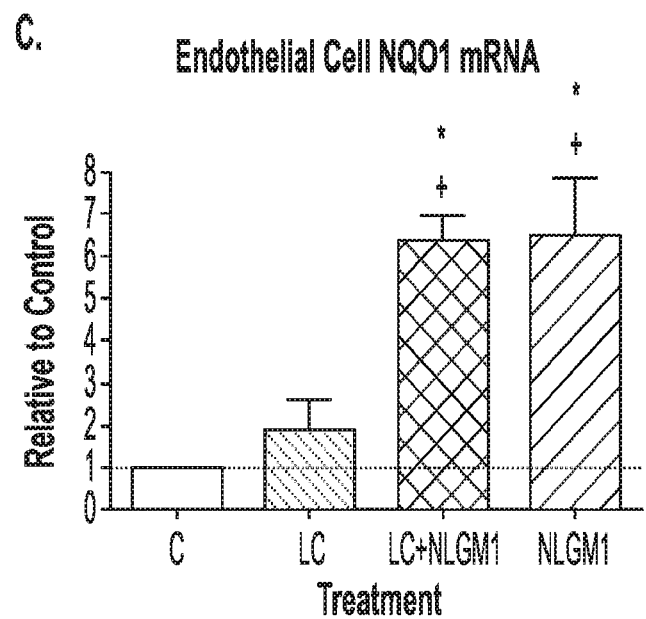
Figure 5D:
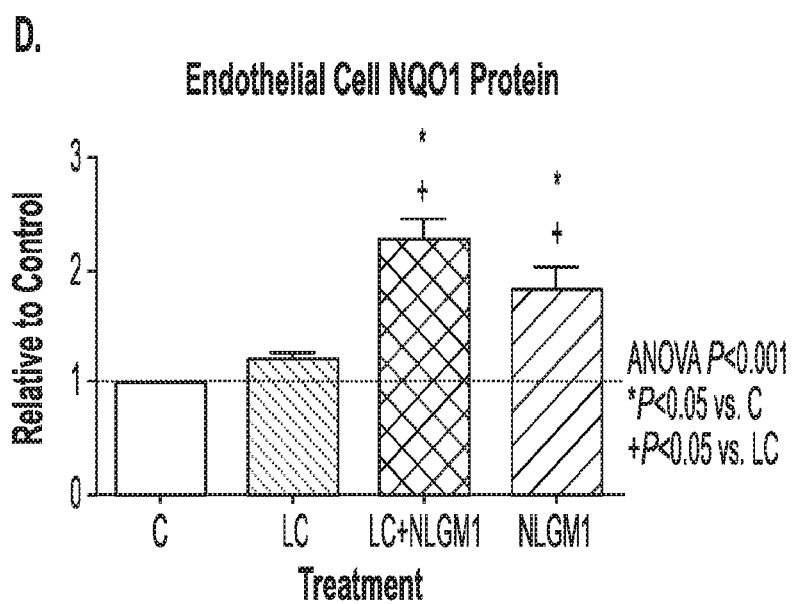

As disclosed herein in the Examples, the results show a trend towards additional impairment of endothelial dysfunction when arterioles were co-treated with Aβ42 and medin (FIG. 2). Importantly, in-vitro experiments show acceleration of fibril (amyloid) formation of Aβ when medin seed is present and vice-versa, suggesting potential synergistic effects between the two proteins.

It was recently shown that Aβ42[11, 12] and medin induce endothelial dysfunction in human leptomeningeal arterioles (see, Examples). As disclosed herein, the Examples show that combined Aβ42 and medin is trending towards worse endothelial dysfunction compared to either peptide alone. Consistent with prior observations that medin amyloid is found in various arterial beds, the data also show that medin is present in brain microvessels of elderly brain donor subjects and may co-localize with Aβ in AD subjects with vascular amyloidosis. This combination of published data and the data described herein support the hypothesis that aging-related dementia may be related to longstanding exposure to prefibrillar amyloid proteins (Aβ and medin) that cause chronic brain microvascular endothelial dysfunction that eventually leads to neurodegeneration (see, for example, FIG. 1).

Nanoliposomes (NLs) are artificial phospholipid vesicles (diameter <100 nm) that can be used for treating amyloid protein disease. Unlike other nanoparticles, NLs are a good choice for human treatment because they are non-toxic, non-immunogenic, fully biodegradable and structurally versatile[13]. First, NLs alone (unconjugated) can bind amyloid proteins with high affinity, reducing cell exposure to amyloid proteins[13, 14]. Second, their surface can be chemically modified, conjugated or "functionalized"[15-40] to allow tissue targeting[41] and intracellular delivery of therapeutic cargo using target specific ligands[42], such as clusterin, a chaperone protein involved in amyloid metabolism. Unconjugated NLs and clusterin-conjugated NLs have been developed and testing has shown human microvascular protection by NLs against toxicity by amyloidogenic light chain proteins (AL amyloidosis)[43, 44]. It has also been shown that phosphatidic acid-containing nanoliposomes prevent fibrillation of Aβ42 in vitro and restores endothelial function in human leptomeningeal arterioles exposed to Aβ42 through reduction of oxidative and nitrative stress[12]. Data disclosed herein shows that NLs also protect microvascular function against medin-induced endothelial dysfunction.

Among therapeutic cargoes by NLs, clusterin may be useful in amyloid injury, for example, in neurodegenerative conditions. Clusterin is an 80-kDa glycoprotein that is found in body fluids and is also a component of high density lipoprotein[45]. There are two isoforms: secretory clusterin (sCLU) that is cytoprotective and prosurvival, and nuclear clusterin (nCLU) which migrates to the nucleus to trigger cell death[46]. As disclosed herein, "clusterin" can refer to the sCLU isoform, which is the form present in commercial human recombinant clusterin protein. Clusterin is a constitutively expressed chaperone glycoprotein that has major dual roles of transporting abnormal proteins (both extracellularly and intracellularly) and is also an important pro-survival protein (by stabilizing bax protein, preventing cytochrome c mitochondria to cytosol translocation and hence reducing apoptosis). The structure and function of clusterin has been reported[47]. A major function of clusterin is its chaperoning capacity for protein stabilization and facilitation of clearance of damaged unfolded proteins[46]. Clusterin is believed to exert an important role in clearing damaged proteins from extracellular spaces and protect against accumulation of aggregated proteins and deposition such as in Alzheimer's disease[46]. Clusterin does not refold proteins but stabilizes stressed proteins into a state which is suitable for refolding by the heat shock proteins such as HSP70[48]. In vitro tests on renal cells demonstrate that clusterin protects against oxidative stress through both aggregative and non-aggregative properties[49]. Cells were protected by clusterin from lipid peroxide formation and monocyte migration induced by oxidized LDL50. Clusterin is more commonly known as a protein associated with Alzheimer's disease in genome-wide association studies; there is also increased clusterin in the plasma of Alzheimer's patients and in amyloid fibrils in brain tissue[47]. However, there is evidence that increased clusterin in Alzheimer's disease reflects a neuroprotective response (albeit overwhelmed by the disease)[51] rather than an etiopathologic effect, since clusterin has been shown to inhibit amyloid formation through Aβ binding[52, 53], to enhance clearance of amyloid aggregates by endocytosis to phagocytes and to prevent apoptosis[47]. It has been demonstrated that clusterin reversed the endothelial dysfunction in human arterioles exposed to amyloidogenic light chain (LC) proteins (from AL light chain amyloidosis patients)[54].

Figures 7A, 7B, 7C, 7D, 7E, 7F, 7G, 7H:
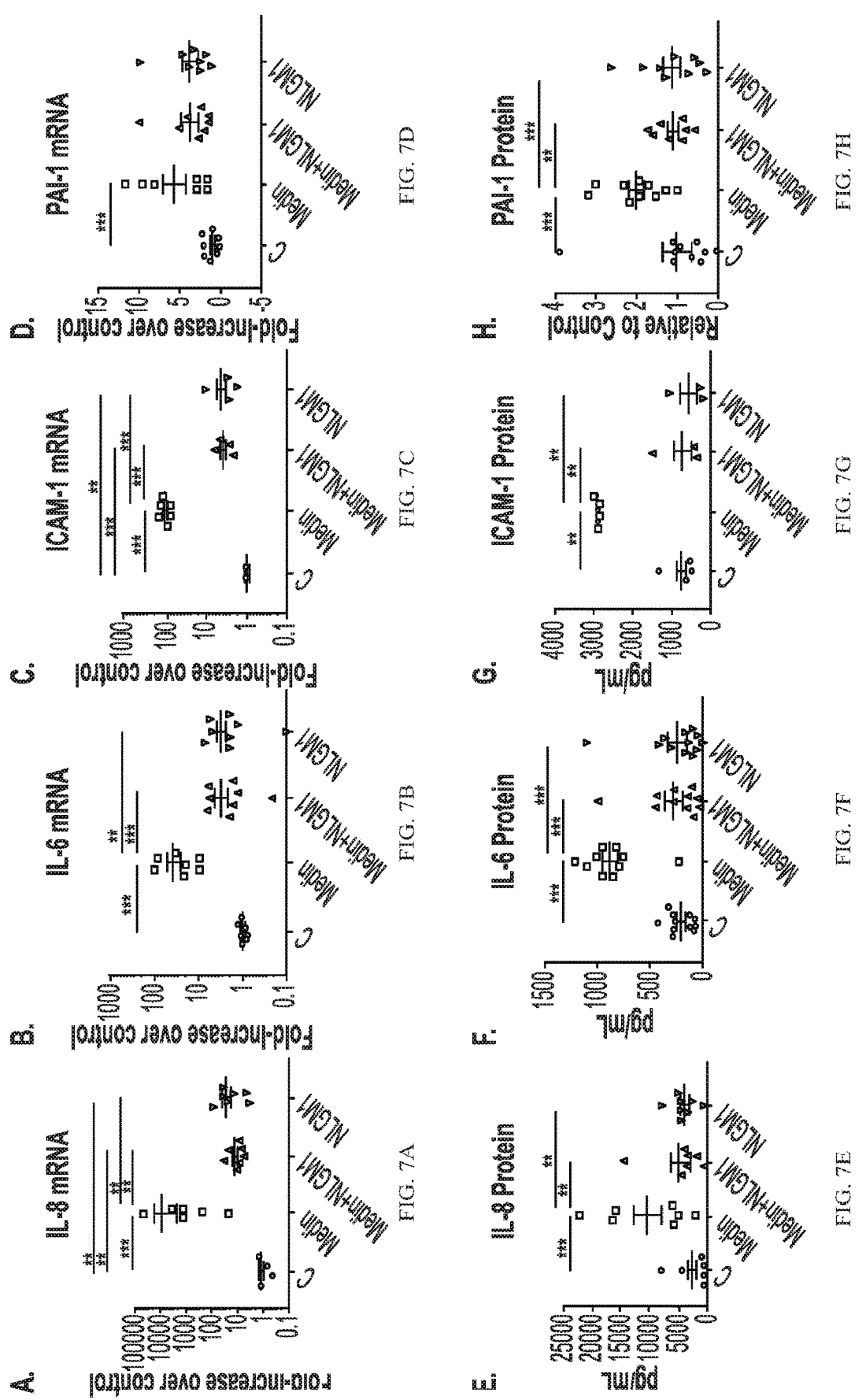
FIGS. 7A-L show that a medin-modifying nanoliposomes, including NLGM1 can protect against medin-induced EC immune activation and reduced viability. Co-treatment of NLGM1 with medin reversed medin-induced increases in gene (A-D) and protein (E-H) expressions of IL-8, IL-6, ICAM-1 and PAI-1, as well as NFκB activation (I).

It has been shown that nanoliposomes composed of phosphatidic acid (PA), cholesterol and phosphatidylcholine (PC) completely restored endothelial function impaired by Aβ42[12], similar to results with AL LC proteins[55]. NLs also reduced endothelial cell internalization of LCs[55] and Aβ42[12]. Atomic force microscopy (AFM) imaging show that NLs physically interact with LCs (FIG. 7) while CD spectroscopy show that NLs alter the amyloid (LC) protein structure[55]. It has also been shown that NLs also completed abrogated Aβ fibril formation (FIG. 8)[12], as well as medin fibrillation.

The results show that GM1-containing NLs induced endothelial cell gene and protein overexpression of antioxidant enzymes heme oxygenase-1 (HO-1) and NAD(P)H dehydrogenase quinone-1 (NQO1) through nuclear factor (erythroid-derived 2)-like 2 (Nrf2) expression (FIG. 7C) and that Nrf2 knockdown abolished the protective effects of NLs against amyloid LC-induced oxidative and nitrative stress[56].

Testing this antioxidant therapeutic pathway to reverse Aβ and medin-induced oxidative and nitrative stress is therefore relevant.

Attempts to formulate NLs (cholesterol and phosphatidylcholine) that are conjugated with clusterin (300 ng/mL), both non-covalently as well as covalently through PEGylation, was successful. When tested in adipose arterioles exposed to amyloid LC proteins, both formulations completely restored endothelial function (max response to acetylcholine: control: 91.6±2%*, LC: 45.8±2.5%, LC+non-covalent clusterin-NL: 75.3±14.2% and LC+covalent clusterin-NL: 80.9±14.5%*, LC+free clusterin: 86.4±3.9%*, *p<0.05 vs. LC). These data support the feasibility of this approach and utility in treating medin and Aβ vasculopathy.

Figure 6A:
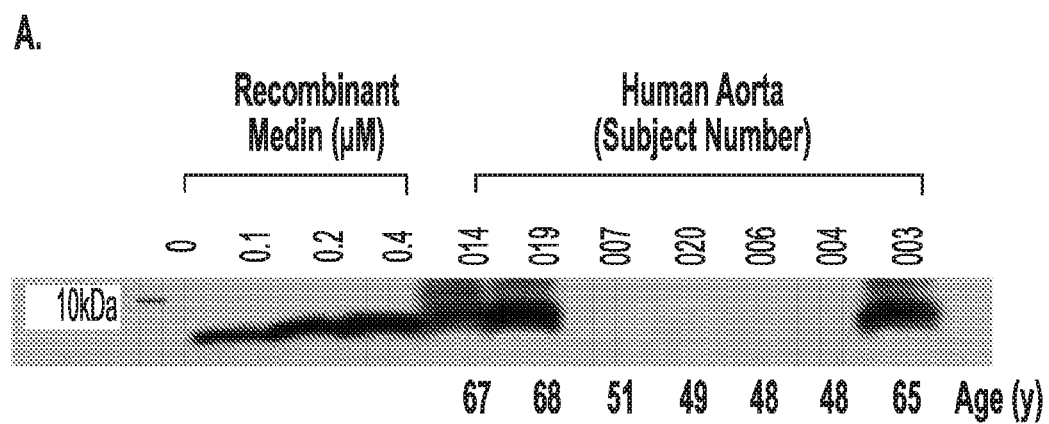
FIGS. 6A-B show that an antibody to medin was used to bind to (A) and quantify amount of medin tissue in aortic tissue (B) with specificity for medin (recombinant medin protein control on left side). Medin accumulates in aortic tissue of subjects >55 but not <55 years of age.
Figure 6B:
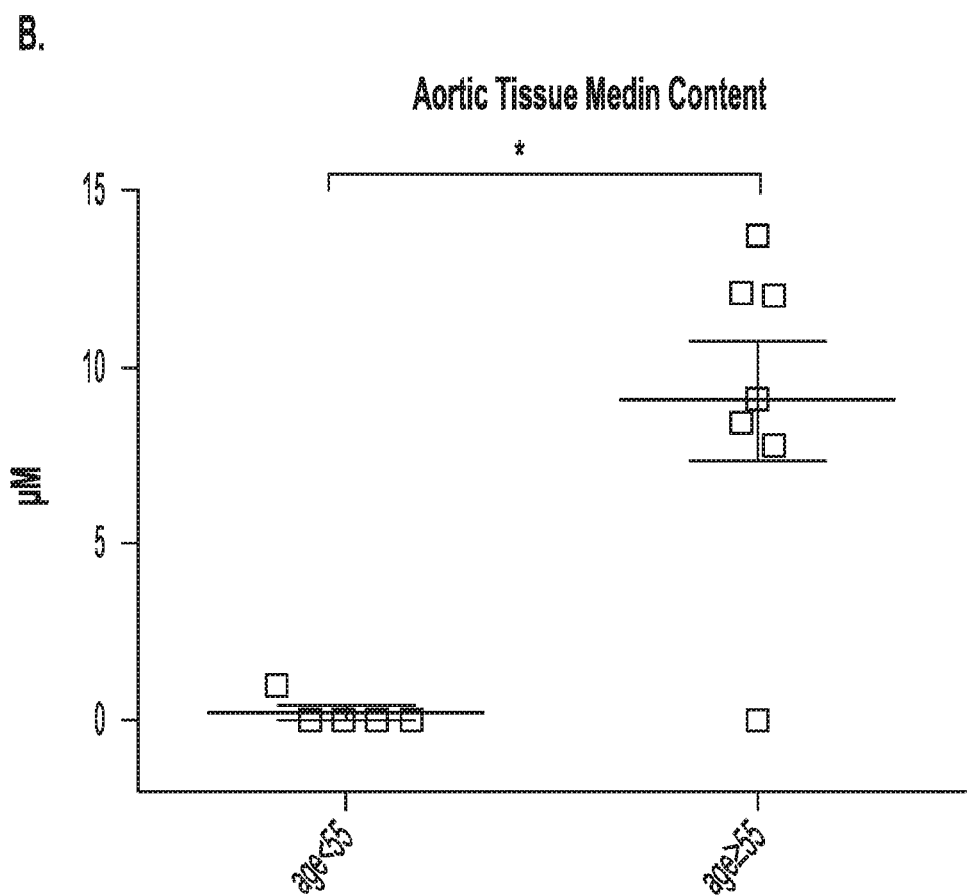

Conclusion. Medin is one of the most common amyloidogenic proteins and tends to aggregate and form amyloid proteins. It is found in various cells and tissues including, but not exclusively, in blood vessels, endothelial cells, smooth muscle cells, glial cells (FIGS. 1 and 10). Both soluble medin (monomer, prefibrillar oligomers) and insoluble medin cause cellular damage, including oxidative and nitrative stress, pro-inflammatory changes and reduced viability. In blood vessels, medin causes vascular dysfunction (endothelial and smooth muscle dysfunction) and inflammation. Data show that both medin (1 μM) and Aβ42 (0.5 μM) caused endothelial, but not smooth muscle dysfunction in human adipose and leptomeningeal (C-D) arterioles compared to control response. Combined medin and Aβ showed a trend towards greater injury (p=NS). Because medin accumulates with aging, it is likely an important mediator of vascular aging (pathologic phenotypic changes associated with aging). Because of its accumulation in cerebrovasculature and effects causing vascular dysfunction, it is likely an important mediator in cerebrovascular disease and dementia disorders. Because of its accumulation in the aorta and peripheral vessels, it is likely an important mediator in aortic degeneration and peripheral and coronary artery disease. Medin accelerates the aggregation of other amyloid proteins, such as beta amyloid. Medin augments the proinflammatory effects of cardiovascular risk factors such as saturated fatty acids such as palmitic acid. There is currently no treatment known to reverse or mitigate adverse effects of medin. Nanoliposomes are phospholipids of various components (such as cholesterol, phosphatidylcholine, monosialoganglioside, phosphatidic acid, etc.) that are <100 nM in size. They are versatile in utility and can be used alone ("naked") or conjugated with therapeutic cargo ("conjugated", such as with clusterin). The results described herein show that nanoliposomes retard the aggregation of medin (FIG. 2), restore human vascular function of vessels exposed to medin, prevent vascular inflammation induced by medin and restore cellular viability (FIG. 7). Based on the results described herein, nanoliposomes of various formulations, both naked and conjugated, may be effective in reversing the cellular and tissue toxicity of medin (FIG. 8). For example, the data disclosed herein show that nanoliposomes of specific formulations (such as monosialoganglioside containing nanoliposomes) induce protective antioxidant cellular responses that will be useful in reversing toxicity of medin and other amyloid proteins inducing oxidative stress (FIG. 5). Further, nanoliposomes may be useful in reversing conditions in which the offending agent/chemical, such as medin, induces cell injury via oxidative stress. The results described herein show that polyclonal antibody to medin specifically binds to medin protein (FIG. 6). Thus, an antibody to medin (either monoclonal or polyclonal, directed to or a portion (or a fragment thereof) of the medin protein) may bind to medin protein, interfere with its biologic functions and prevent medin-induced cell and tissue toxicity. Because medin is involved in aging related degenerative diseases such as atherosclerosis and dementia disorders, nanoliposomes and anti-medin antibodies by reversing medin induced injury may be useful treatment for these diseases.

REFERENCES

1. Haggqvist B, Naslund J, Sletten K, Westermark G T, Mucchiano G, Tjernberg L O, Nordstedt C, Engstrom U, Westermark P. Medin: an integral fragment of aortic smooth muscle cell-produced lactadherin forms the most common human amyloid. *Proceedings of the National Academy of Sciences of the United States of America* 1999; 96:8669-8674.
2. Larsson A, Soderberg L, Westermark G T, Sletten K, Engstrom U, Tjernberg L O, Naslund J, Westermark P. Unwinding fibril formation of medin, the peptide of the most common form of human amyloid. *Biochem Biophys Res Commun* 2007; 361:822-828.
3. Peng S, Glennert J, Westermark P. Medin-amyloid: a recently characterized age-associated arterial amyloid form affects mainly arteries in the upper part of the body. *Amyloid: the international journal of experimental and clinical investigation: the official journal of the International Society of Amyloidosis* 2005; 12:96-102.
4. Peng S, Larsson A, Wassberg E, Gerwins P, Thelin S, Fu X, Westermark P. Role of aggregated medin in the pathogenesis of thoracic aortic aneurysm and dissection. *Laboratory investigation; a journal of technical methods and pathology* 2007; 87:1195-1205.
5. Peng S, Westermark G T, Naslund J, Haggqvist B, Glennert J, Westermark P. Medin and medin-amyloid in ageing inflamed and non-inflamed temporal arteries. *The Journal of pathology* 2002; 196:91-96.
6. Mucchiano G, Cornwell G G, 3rd, Westermark P. Senile aortic amyloid. Evidence for two distinct forms of localized deposits. *The American journal of pathology* 1992; 140:871-877.
7. Davies H A, Phelan M M, Wilkinson M C, Migrino R Q, Truran S, Franco D A, Liu L N, Longmore C J, Madine J. Oxidative Stress Alters the Morphology and Toxicity of Aortic Medial Amyloid. *Biophys J* 2015; 109:2363-2370.
8. Lakatta E G. The reality of aging viewed from the arterial wall. *Artery research* 2013; 7:73-80.
9. Larsson A, Peng S, Persson H, Rosenbloom J, Abrams W R, Wassberg E, Thelin S, Sletten K, Gerwins P, Westermark P. Lactadherin binds to elastin—a starting point for medin amyloid formation? *Amyloid: the international journal of experimental and clinical investigation: the official journal of the International Society of Amyloidosis* 2006; 13:78-85.
10. Migrino R Q, Truran S, Karamanova N, Franco D A, Davies H A, Burciu C, Madine J. Human microvascular endothelial dysfunction induced by amyloidogenic medin. 2016 American College of Cardiology Scientific Sessions. Chicago, IL, 2016.
11. Truran S, Franco D A, Roher A E, Beach T G, Burciu C, Serrano G, Maarouf C L, Schwab S, Anderson J, Georges J, Reaven P, Migrino R Q. Adipose and leptomeningeal arteriole endothelial dysfunction induced by beta-amyloid peptide: a practical human model to study Alzheimer's disease vasculopathy. *Journal of neuroscience methods* 2014; 235:123-129.

12. Truran S, Weissig V, Madine J, Davies H A, Guzman-Villanueva D, Karamanova N, Serrano G, Beach T G, Migrino R Q. Nanoliposomes protect against human arteriole endothelial dysfunction induced by B-amyloid peptide. *J Cereb Blood Flow Metab* 2015; 36:405-412.
13. Re F, Cambianica I, Sesana S, Salvati E, Cagnotto A, Salmona M, Couraud P O, Moghimi S M, Masserini M, Sancini G. Functionalization with ApoE-derived peptides enhances the interaction with brain capillary endothelial cells of nanoliposomes binding amyloid-beta peptide. *J Biotechnol* 2011; 156:341-346.
14. Gobbi M, Re F, Canovi M, Beeg M, Gregori M, Sesana S, Sonnino S, Brogioli D, Musicanti C, Gasco P, Salmona M, Masserini M E. Lipid-based nanoparticles with high binding affinity for amyloid-beta1-42 peptide. *Biomaterials* 2010; 31:6519-6529.
15. Asahi M, Rammohan R, Sumii T, Wang X, Pauw R J, Weissig V, Torchilin V P, Lo E H. Antiactin-targeted immunoliposomes ameliorate tissue plasminogen activator-induced hemorrhage after focal embolic stroke. *J Cereb Blood Flow Metab* 2003; 23:895-899.
16. Boddapati S V, D'Souza G G, Erdogan S, Torchilin V P, Weissig V. Organelle-targeted nanocarriers: specific delivery of liposomal ceramide to mitochondria enhances its cytotoxicity in vitro and in vivo. *Nano Lett* 2008; 8:2559-2563.
17. Boddapati S V, D'Souza G G, Weissig V. Liposomes for drug delivery to mitochondria. *Methods Mol Biol* 2010; 605:295-303.
18. Boddapati S V, Tongcharoensirikul P, Hanson R N, D'Souza G G, Torchilin V P, Weissig V. Mitochondriotropic liposomes. *J Liposome Res* 2005; 15:49-58.
19. D'Souza G G, Rammohan R, Cheng S M, Torchilin V P, Weissig V. DQAsome-mediated delivery of plasmid DNA toward mitochondria in living cells. *J Control Release* 2003; 92:189-197.
20. Elbayoumi T, Weissig V. Implications of intracellular distribution of nanovesicles for bioimaging studies. *J Biomed Nanotechnol* 2009; 5:620-633.
21. Niedermann G, Weissig V, Sternberg B, Lasch J. Carboxyacyl derivatives of cardiolipin as four-tailed hydrophobic anchors for the covalent coupling of hydrophilic proteins to liposomes. *Biochimica et biophysica acta* 1991; 1070:401-408.
22. Patel N R, Hatziantoniou S, Georgopoulos A, Demetzos C, Torchilin V P, Weissig V, D'Souza G G. Mitochondria-targeted liposomes improve the apoptotic and cytotoxic action of sclareol. *J Liposome Res* 2009; 20:244-249.
23. Schreier H, Ausborn M, Gunther S, Weissig V, Chander R. (Patho)physiologic pathways to drug targeting: artificial viral envelopes. *J Mol Recognit* 1995; 8:59-62.
24. Tan L, Weissig V, Gregoriadis G. Comparison of the immune response against polio peptides covalently-surface-linked to and internally-entrapped in liposomes. *Asian Pac J Allergy Immunol* 1991; 9:25-30.
25. Torchilin V P, Khaw B A, Weissig V. Intracellular targets for DNA delivery: nuclei and mitochondria. *Somat Cell Mol Genet* 2002; 27:49-64.
26. Torchilin V P, Rammohan R, Weissig V, Levchenko T S. TAT peptide on the surface of liposomes affords their efficient intracellular delivery even at low temperature and in the presence of metabolic inhibitors. *Proceedings of the National Academy of Sciences of the United States of America* 2001; 98:8786-8791.
27. Torchilin V P, Weissig V. Liposomes. Oxford University Press, 2003.
28. Truran S, Weissig V, Franco D A, Maltagliati A, Burciu C, Liu J, Migrino R Q. Nanoliposomes restore endothelial function of human adipose arterioles exposed to AL amyloidosis light chain proteins. Experimental Biology 2012. San Diego CA, 2012.
29. Weissig V. Mitochondrial-targeted drug and DNA delivery. *Crit Rev Ther Drug Carrier Syst* 2003; 20:1-62.
30. Weissig V. Liposomes: Methods and Protocols (Springer Protocols). Humana Press, 2010.
31. Weissig V, Boddapati S V, Cheng S M, D'Souza G G. Liposomes and liposome-like vesicles for drug and DNA delivery to mitochondria. *J Liposome Res* 2006; 16:249-264.
32. Weissig V, Lasch J, Erdos G, Meyer H W, Rowe T C, Hughes J. DQAsomes: a novel potential drug and gene delivery system made from Dequalinium. *Pharm Res* 1998; 15:334-337.
33. Weissig V, Lasch J, Gregoriadis G. Covalent coupling of sugars to liposomes. *Biochimica et biophysica acta* 1989; 1003:54-57.
34. Weissig V, Lasch J, Gregoriadis G. A method for preparation of liposomes with encapsulated peptide antigens and surface-linked sugar residues. *Pharmazie* 1991; 46:56-57.
35. Weissig V, Lasch J, Klibanov A L, Torchilin V P. A new hydrophobic anchor for the attachment of proteins to liposomal membranes. *FEBS Lett* 1986; 202:86-90.
36. Weissig V, Lizano C, Torchilin V P. Selective DNA release from DQAsome/DNA complexes at mitochondria-like membranes. *Drug Deliv* 2000; 7:1-5.
37. Weissig V, Torchilin V P. Mitochondriotropic cationic vesicles: a strategy towards mitochondrial gene therapy. *Curr Pharm Biotechnol* 2000; 1:325-346.
38. Weissig V, Torchilin V P. Cationic bolasomes with delocalized charge centers as mitochondria-specific DNA delivery systems. *Adv Drug Deliv Rev* 2001; 49:127-149.
39. Weissig V, Whiteman K R, Torchilin V P. Accumulation of protein-loaded long-circulating micelles and liposomes in subcutaneous Lewis lung carcinoma in mice. *Pharm Res* 1998; 15:1552-1556.
40. Weissig V V, Babich J, Torchilin V V. Long-circulating gadolinium-loaded liposomes: potential use for magnetic resonance imaging of the blood pool. *Colloids Surf B Biointerfaces* 2000; 18:293-299.
41. Coelho T, Adams D, Silva A, Lozeron P, Hawkins P N, Mant T, Perez J, Chiesa J, Warrington S, Tranter E, Munisamy M, Falzone R, Harrop J, Cehelsky J, Bettencourt B R, Geissler M, Butler J S, Sehgal A, Meyers R E, Chen Q, Borland T, Hutabarat R M, Clausen V A, Alvarez R, Fitzgerald K, Gamba-Vitalo C, Nochur S V, Vaishnaw A K, Sah D W, Gollob J A, Suhr O B. Safety and efficacy of RNAi therapy for transthyretin amyloidosis. *N Engl J Med* 2013; 369:819-829.
42. Bhaskar S, Tian F, Stoeger T, Kreyling W, de la Fuente J M, Grazu V, Borm P, Estrada G, Ntziachristos V, Razansky D. Multifunctional Nanocarriers for diagnostics, drug delivery and targeted treatment across blood-brain barrier: perspectives on tracking and neuroimaging. *Part Fibre Toxicol* 2010; 7:3.
43. Franco D A, Truran S, Weissig V, Burciu C, Maltagliati A, Murarka S, Hari P, Migrino R Q. Clusterin-nanoliposome complex attenuates human arteriole endothelial dysfunction induced by AL amyloid light chain proteins. American Heart Association 2012 Scientific Sessions. Los Angeles CA, 2012.
44. Truran S, Weissig V, Ramirez-Alvarado M, Franco D A, Burciu C, Georges J G, Murarka S, Okoth W A, Hari P, Migrino R Q. Nanoliposomes protect against amyloid-light chain protein-induced endothelial injury. *J Liposome Res* 2013.
45. Klock G, Baiersdorfer M, Koch-Brandt C. Chapter 7: Cell protective functions of secretory Clusterin (sCLU). *Adv Cancer Res* 2009; 104:115-138.
46. Trougakos I P, Djeu J Y, Gonos E S, Boothman D A. Advances and challenges in basic and translational research on clusterin. *Cancer Res* 2009; 69:403-406.
47. Nuutinen T, Suuronen T, Kauppinen A, Salminen A. Clusterin: a forgotten player in Alzheimer's disease. *Brain Res Rev* 2009; 61:89-104.
48. Poon S, Easterbrook-Smith S B, Rybchyn M S, Carver J A, Wilson M R. Clusterin is an ATP-independent chaperone with very broad substrate specificity that stabilizes stressed proteins in a folding-competent state. *Biochemistry* 2000; 39:15953-15960.
49. Schwochau G B, Nath K A, Rosenberg M E. Clusterin protects against oxidative stress in vitro through aggregative and nonaggregative properties. *Kidney Int* 1998; 53:1647-1653.
50. Navab M, Hama-Levy S, Van Lenten B J, Fonarow G C, Cardinez C J, Castellani L W, Brennan M L, Lusis A J, Fogelman A M, La Du B N. Mildly oxidized LDL induces an increased apolipoprotein J/paraoxonase ratio. *J Clin Invest* 1997; 99:2005-2019.
51. Schrijvers E M, Koudstaal P J, Hofman A, Breteler M M. Plasma clusterin and the risk of Alzheimer disease. *JAMA* 2011; 305:1322-1326.
52. Bell R D, Sagare A P, Friedman A E, Bedi G S, Holtzman D M, Deane R, Zlokovic B V. Transport pathways for clearance of human Alzheimer's amyloid beta-peptide and apolipoproteins E and J in the mouse central nervous system. *J Cereb Blood Flow Metab* 2007; 27:909-918.
53. Yerbury J J, Poon S, Meehan S, Thompson B, Kumita J R, Dobson C M, Wilson M R. The extracellular chaperone clusterin influences amyloid formation and toxicity by interacting with prefibrillar structures. *FASEB journal: official publication of the Federation of American Societies for Experimental Biology* 2007; 21:2312-2322.
54. Franco D A, Truran S, Burciu C, Gutterman D D, Maltagliati A, Weissig V, Hari P, Migrino R Q. Protective role of clusterin in preserving endothelial function in AL amyloidosis. *Atherosclerosis* 2012; 225:220-223.
55. Truran S, Weissig V, Ramirez-Alvarado M, Franco D A, Burciu C, Georges J, Murarka S, Okoth W A, Schwab S, Hari P, Migrino R Q. Nanoliposomes protect against AL amyloid light chain protein-induced endothelial injury. *J Liposome Res* 2014; 24:69-73.
56. Franco D A, Weissig V, Karamanova N, Truran S, Guzman-Villanueva D, Ramirez-Alvarado M, Blancas-Mejia L M, Migrino R Q. Monosialoganglioside-containing nanoliposomes protect against AL amyloidosis light chain induced endothelial injury through Nrf2 defense pathway. 2016 Experimental Biology. San Diego CA, 2016.

Example 2: Endothelial Immune Activation by Medin: A Role in Cerebrovascular Disease and Reversal by Monosialoganglioside-Containing Nanoliposomes Objective: The function of medin, one of the most common human amyloid proteins that accumulates in the vasculature with aging, remains unknown. Described herein are studies that show medin's role in cerebrovascular disease (CVD) by comparing cerebral arteriole medin content between cognitively normal (CN) and vascular dementia (VaD) patients and studying its effects on endothelial cell (EC) immune activation and neuroinflammation. Also tested was whether a medin-modifying nanoliposomes (monosialoganglioside-containing nanoliposomes (NLGM1)) could reverse medin's adverse effects.

Approach: Cerebral collateral arteriole medin and astrocyte activation were measured and compared between vascular dementia (VaD) and cognitively normal (CN) elderly brain donors. ECs were exposed to physiologic dose of medin (5 μM) and viability and immune activation (interleukin [IL]-8, IL-6, intercellular adhesion molecule [ICAM]-1 and plasminogen activator inhibitor-1 [PAI-1]) were measured without or with NLGM1 (300 μg/mL). Astrocytes were exposed to vehicle, medin, medin-treated ECs or their conditioned media, and IL-8 production compared.

Results: Cerebral arteriole medin, white matter lesion scores and astrocyte activation were higher in VaD versus CN donors. Medin induced EC immune activation (increased IL-8, IL-6, ICAM-1 and PAI-1) and reduced EC viability that were reversed by NLGM1. IL-8 production was augmented when astrocytes were exposed to medin-treated ECs or their conditioned media.

Conclusions: Cerebral arteriole medin is higher in vascular dementia compared to cognitively normal patients. Medin induces endothelial cell immune activation that modulates astrocyte activation and its effects are reversed by NLGM1. Medin is a risk factor for aging-related CVD and vascular dementia.

The results described herein demonstrate that medin is quantified for the first time in human cerebral arterioles and was higher in vascular dementia patients compared to cognitively normal subjects. Endothelial cells exposed to physiologic doses of medin show increased oxidative stress, reduced viability and immune activation that are reversed by co-treatment with monosialoganglioside nanoliposomes. The protective effect of NLGM1 is based on Nrf-2 activation and inhibition of NFκB. Astrocyte IL-8 production is augmented in presence of medin-treated endothelial cells or their conditioned media, suggesting role in modulating neuro inflammation.

Introduction. Age is an important risk factor for cerebrovascular disease (CVD) and cognitive dysfunction disorders, including vascular dementia (VaD)[1]. Even in the absence of traditional cardiovascular risk factors, aging results in well-defined vascular phenotypic changes including endothelial dysfunction[2] and chronic indolent low grade inflammation leading to atherosclerosis and CVD[3]. Although the molecular, functional and structural changes of aging-related CVD have been documented[3], the specific intrinsic biologic determinants of these changes remain largely unknown. Medin, a 50-amino acid peptide, forms one of the most common types of human amyloid[4,5] and accumulates in the vasculature with aging[6-9] yet its biologic effects are still largely unknown. It is a cleavage product from parent protein milk fat globule-EGF factor 8 protein[4]. It is widely known to be present in aging aorta[4] with little to no aortic medin in patients <55 years old and increased in those ≥55 years old[6], but the extent or degree of accumulation in cerebral vessels has not been reported. It was previously reported that treatment with physiologic doses of medin induced endothelial dysfunction in human peripheral and cerebral arterioles mediated by oxidative and nitrative stress[6,10]. It was also shown that medin increased pro-inflammatory cytokine production by endothelial cells (ECs). These findings support a role of medin as an agent in vascular aging pathology leading to CVD. Furthermore, medin's effect on the vasculature could influence the perivascular milieu. In VaD, neuroinflammation occurs proximate to cerebral arterioles. Activated astrocytes and microglia, cellular markers of neuroinflammation, are commonly found in regions of white matter changes' concentrating around blood vessels[12]. This suggests tight vasculo-neural inflammatory coupling. Cerebral white matter lesions (CWML) in aging and neurodegenerative diseases such as VaD represent microvascular ischemic changes associated with both endothelial and glial activation[13] that are highly associated with dementia and stroke[14]. Neuroinflammation by itself can contribute to neurodegeneration and cognitive dysfunction in VaD and Alzheimer's disease[12][15]. Therefore, the initiation or aggravation of neuroinflammation by vascular inflammation could be a mechanism explaining the tight link among aging, CVD and dementia disorders. The experiments described herein evaluated medin's role in CVD by comparing cerebral arteriole medin content between cognitively normal (CN) and VaD patients and studying its effects on EC immune activation and modulation of neuroinflammation.

Previously it was shown that nanoliposomes (artificial phospholipid vesicles <100 nm in diameter) that contain monosialogangliosides (NLGM1) or phosphatidic acid prevented endothelial dysfunction induced by other amyloid proteins, specifically AL amyloid light chain proteins[16] or β-amyloid[17], respectively. It was also tested whether NLGM1 could reverse medin's adverse effects while identifying potential mechanisms for the protection.

Materials and Methods. Medin and monosialoganglioside nanoliposomes. Recombinant medin was used for treatment conditions in the study. Medin was expressed in Lemo 21 (DE3) cells using pOPINS-medin[6,16]. Medin was confirmed to have >95% purity by sodium dodecyl sulfate polyacrylamide gel electrophoresis and characterized by matrix-assisted laser desorption as well as ionization mass spectrometry. Endotoxin levels were confirmed to be <0.5 ng/ml using Limulus Amebocyte Lysate assay (Pierce, Dallas TX).

NLGM1 was prepared from phosphatidylcholine, cholesterol and monosialoganglioside (molar ratios 70:25:5) using lipid film hydration method[14]. Lipid components were dissolved in chloroform and the solvent was removed by drying in a rotary vacuum evaporator until a thin lipid film was formed. This lipid film was hydrated with HEPES solution (pH 7.4) to obtain a final lipid concentration of 10 mg/ml. This liposomal suspension was sonicated for 45 minutes (Sonic Dismembrator Model 100, Fisher Scientific) in an ice bath until an opaque solution was formed, which indicates the formation of small unilamellar vesicles (nanoliposomes). To precipitate and remove titanium particles sloughed off from the probe during sonication, NLGM1 were centrifuged at 101 g for 15 minutes at 4° C.

Brain tissue sources, Western blot and histopathology. Donors gave informed consent for post-mortem brain donation under the Brain and Body Donation Program[18]. Cerebral collateral arterioles from CN and VaD participants were isolated from leptomeninges following rapid autopsy (post-mortem interval 3.4±0.2 hours). VaD diagnosis was adjudicated using NINDS-AIRENS criteria[19]. CN was the diagnosis if there was no cognitive dysfunction and if there was age-consistent neuropathology[18]. Tissue handling details were reported previously[6]. In brief, tissues were immediately placed in sterile HEPES buffer (4° C., pH 7.4). Arterioles were isolated and homogenized in tissue lysis buffer (RIPA or TBS-TritonX100 1%). Tissue samples (60 μg of protein determined by Bradford assay) and recombinant medin (0.01, 0.1, 0.5 μg) were loaded for electrophoresis and Western blot performed[20]. Primary antibody against medin (18G1, 1:500, generously provided by Prothena Biosciences Limited, Dublin Ireland) and 800 CW infrared fluorescent conjugated goat secondary antibody (Li-COR Biosciences, Lincoln NE) were used. Bands were detected using Li-COR Odyssey CLx system (Image Studio 4.0) and normalized to β-actin loading control. A standard curve was plotted using the medin samples and used to calculate tissue medin content.

CWML are known to be caused by cerebral small vessel disease and is important in the pathophysiology of VaD and other dementia disorders[21]. The brain sources of cerebral collateral arterioles were scored for CWML using 4% formaldehyde-treated tissue slices[22]. In brief, a score of 1 denotes CWML restricted to the immediate periventricular area occupying less than a third of the centrum semiovale, 2 denotes involvement of one-third to two-thirds while 3 denotes involvement of more than two-thirds of the centrum semiovale. The scores in the frontal, temporal, parietal and occipital regions were added to obtain the CWML total score and compared between CN and VaD donors. Arteriole medin content was also compared between donors with high (≥median value) versus low (<median value) CWML scores.

Paraformaldehyde-treated, paraffin-embedded middle frontal gyrus tissues from CN and VaD donors (5 μm sections) were analyzed. Astrocyte activation was assessed by immunohistochemistry using anti-glial fibrillary acidic protein (GFAP) primary antibody (1:150, Cell Signaling Technology), horse radish peroxidase conjugated secondary antibody and 3, 3-diaminobenzidine (DAB) staining and co-stained with hematoxylin-eosin. Imaging was performed on a Biotek Cytation 5 (Winooski VT) and DAB-positive cells were manually counted from 5 areas uniformly spaced around a central beacon set by operator. In randomly selected CN and VaD donors (N=3 each), GFAP-expressing astrocytes were counted ≤100 μm and >100 μm from cerebral arterioles.

Endothelial cell immune activation. Primary culture human umbilical vein ECs (passages 4-8, Lonza, Walkersville MD) were seeded into 6-well plates and grown to full confluence. Human umbilical vein ECs have been extensively used to study vascular cell behavior in neurodegenerative disease studies such as AD and VaD as they show similarity in properties as brain ECs, including Aβ metabolism[23,24], expression of tight junction proteins[25] and metabolic interactions with neural cells[26]. ECs were exposed to 20 hours of vehicle or medin (5 μM, dose chosen as this was the mean medin concentration found in human vascular tissue) without or with NLGM1 (300 μM). Additional replicates were also treated with NLGM1 (300 μM) plus transcription factor nuclear factor erythroid 2-related factor 2 (Nrf2) inhibitor brusatol (1 μM). EC immune activation was assessed using gene and protein expressions of inflammation-related cytokines/chemokines interleukin (IL)-8, IL-6, intercellular adhesion molecule (ICAM)-1 and plasminogen activator inhibitor (PAI)-1 (primers from IDT DNA Technologies, Coralville IL)[6,16]. Following lysis, RNA was extracted and converted to cDNA using Aurum Total RNA Mini Kit and iScript cDNA synthesis kit (Bio-Rad Laboratories, Coralville IA) with β-actin as reference normalization gene normalization. It was previously showed that medin-induced increase in EC IL-8 and IL-6 were nuclear factor-kappa B (NFκB)-mediated, and to confirm whether effects on ICAM-1 and PAI-1 were also NFκB-mediated, medin was also co-treated with a specific small molecule inhibitor of NFκB[27], RO106-9920 (100 μM, Tocris Biosciences, Bristol UK) in additional replicates.

The conditioned cell media from treated ECs were analyzed for IL-8 and IL-6 protein by enzyme linked immunosorbent assay (ELISA) using DuoSet kit (R&D Systems, Minneapolis MN). ICAM-1 protein was measured from whole cell lysate using ICAM-1 ELISA kit (R&D Systems). PAI-1 and phosphorylated NFκB (phospho-NFκB p65, Ser536, 93H1) proteins were measured using Western blot (1:500, Cell Signaling Technology, Danvers MA).

Endothelial cell viability and oxidative stress. Treated ECs were incubated (15 minutes) with dihydroethidium (5 μmol/L, Molecular Probes) to assess superoxide[28], calcein-acetoxymethyl (AM, 10 nmol/L, Life Technologies)[29], annexin V-FITC (0.5 μg/ml, eBiosciences, San Diego CA) or propidium iodide (0.15 μM, Sigma-Aldrich)[30] to assess cell viability using flow cytometer (Beckman Coulter FC500, Indianapolis IN) at the following excitation/emission settings: 490/626 (dihydroethidium), 494/517 (calcein-AM), 488/525 (annexin V) and 488/620 nm (propidium iodide).

Activated Nrf-2 protein was measured by separating the nuclear from cytosolic components using NE-PER Nuclear and Cytoplasmic Extraction kit (Thermo Scientific, Rockford IL) and using anti-Nrf2 primary antibody (1:500, Cell Signaling) on nuclear proteins using Western blot with tubulin as loading control. Heme oxygenase (HO)-1 and NAD(P)H Quinone dehydrogenase 1 (NQO1) proteins were measured from whole cell lysates using anti-HO-1 (1:1000, Cell Signaling Technology) and anti-NQO1 (1:1000, Cell Signaling) primary antibodies.

Astrocyte monoculture. Human primary astrocytes (passage 3, Gibco, Madison WI) were seeded in gelatin matrix ($4\times10^4$ cells/cm$^2$) coated plates, allowed to attach overnight and exposed for 20 hours to vehicle, medin (5 μM), conditioned media from vehicle-treated ECs (10% vol/vol exchange) or conditioned media from medin (5 μM)-treated ECs. Conditioned media IL-8 were measured by ELISA.

Microfluidic chip fabrication and 3D chip astrocyte and endothelial cell coculture. The microfluidic platform was fabricated in polydimethylsiloxane (PDMS) using standard SU-8 photolithography and replica molding technique, consisting of two side channels for seeding of endothelial cells (ECs) and a central region for astrocyte culture. The dimensions of the side channels' (length, width and height, are 4 mm, 250 μm and 200 μm respectively. The width of the 3D central region is 2 mm Elliptical micro-posts were localized within the central tissue region (500 um width, 100 um height) with specific micro-post spacing to optimize alignment of the astrocytes, while maintaining cellular connectivity and paracrine signaling. Creation of the master silicon wafer through photolithography was executed through spin-coating of SU-8 on a wafer to a height of 200 μm. The wafer was soft-baked, then exposed to UV through a transparent photomask with the chip design. After post-baking, the developed wafer was used as the substrate for soft lithography with PDMS replica molding. A PDMS base: curing agent ratio of 10:1 was used. Then, the PDMS channels were bonded to glass slides through oxygen plasma. The PDMS-glass bonded device was sterilized through autoclave, and subsequently the main tissue channel was surface treated to create an adhesive layer for attachment of ECM (collagen) hydrogel. First, poly D-lysine (1 mg/mL) was inserted into the main channel, and incubated at 37° C., 5% CO2 for 45 minutes. The main channel was washed with DI water, then 1% glutaraldehyde was inserted, and the device was incubated at room temperature for 1 hour and 45 minutes. The devices were then thoroughly washed with DI water and baked at 80° C. overnight for dehydration.

Human umbilical vein ECs were seeded into the side channels ($2\times10^6$ cells/mL in EC media) overnight. Human primary astrocytes ($10\times10^6$ cells/mL) were embedded in collagen type I (rat tail) hydrogel (1 mg/mL) and injected into the central channel. Media was changed every 24 hours with combination of 50:50 astrocyte: EC media. Formation of EC monolayer and 3D astrocyte tissue was confirmed after 72 hours, then vehicle or medin (5 μM) was infused (20 hours) on side channels of chips containing astrocytes and ECs, and chips with astrocytes but no ECs. Conditioned media IL-8 were measured using ELISA.

Data analyses. Data are expressed as mean±standard error of means and significant p-value set at p<0.05 (two-sided). Paired group analyses were done using paired t-test (2 groups), or one-way repeated measures analysis of variance (>2 groups) with pairwise post-hoc analysis using Holm-Sidak. For data that do not have normal distribution or equal variance, natural log (Ln) or square root transformation was performed, and analyses done using normally distributed transformed data. If data remained non-normally distributed, Wilcoxon signed rank test (2 groups) or one-way repeated measures ANOVA on ranks (>2 groups) with Dunn's post-hoc pairwise testing was performed. Proportions were compared using Fisher's exact test. Unpaired groups were compared using unpaired t-test. Analyses were done using Sigmastat 3.5 (Systat, San Jose CA).

Results. Human cerebral arteriole medin is higher in VaD versus CN donors. To assess relevance of medin in CVD, cerebral collateral arterioles were collected from rapid autopsy of clinico-histopathologically confirmed VaD (N=11, 89±3 years old, 9 females) and CN brain donors (N=12, 82±4 years old, 4 females, p=NS for age and gender) and quantified arteriole medin content. Overall cerebral arteriole medin was 5.9±1.2 ng medin/μg arteriole protein (32±10 μM). Arteriole medin was significantly higher in VaD compared to CN donors. CWML score was significantly higher in VaD versus CN donors. Donors with higher CWML scores (≥median value) had significantly increased arteriole medin compared to donors with lower scores. To assess degree of neuroinflammation, GFAP-expressing astrocytes, a marker of astrocyte activation[31], were measured in the middle frontal gyrus. Activated astrocytes were significantly higher in VaD versus CN brains. Additionally, astrocytes aggregated around cerebral arterioles, with 73.5±5% of astrocytes within 100 μm of a cerebral arteriole versus 26.5±5%>100 μM (p=0.007).

Medin induces endothelial cell immune activation and cytotoxicity Immune activation and viability was assessed in ECs following 20-hour medin treatment. The dose selected (5 μM) is within physiologic range of concentration found in human cerebral arterioles based on results (32±10 μM). The data show that show that medin causes EC immune activation and reduced viability. Exposure to medin significantly induced increased EC gene and protein expressions of IL-8, IL-6, ICAM-1 and PAI-1, with log-fold increases in IL-8, IL-6 and ICAM-1. Medin also caused significantly reduced EC viability based on reduced calcein-AM and increased annexin-V and propidium iodide fluorescence.

The results show that medin induces NFκB activation (phosphorylated NFκB) in ECs starting at 15 minutes, peaks at 1 hour and persists for 20 hours post-exposure. Co-treatment with RO106-9920, a specific small molecule inhibitor of NFκB-dependent cytokine expression[27] abolished medin-induced increased gene expression of IL-8, IL-6, ICAM-1 and PAI-1, confirming that immune activation is NFκB-dependent. Interestingly, co-treatment of medin with NFκB inhibitor did not improve EC viability suggesting that cytotoxicity is not NFκB-dependent.

Figures 7I, 7J, 7K, 7L:
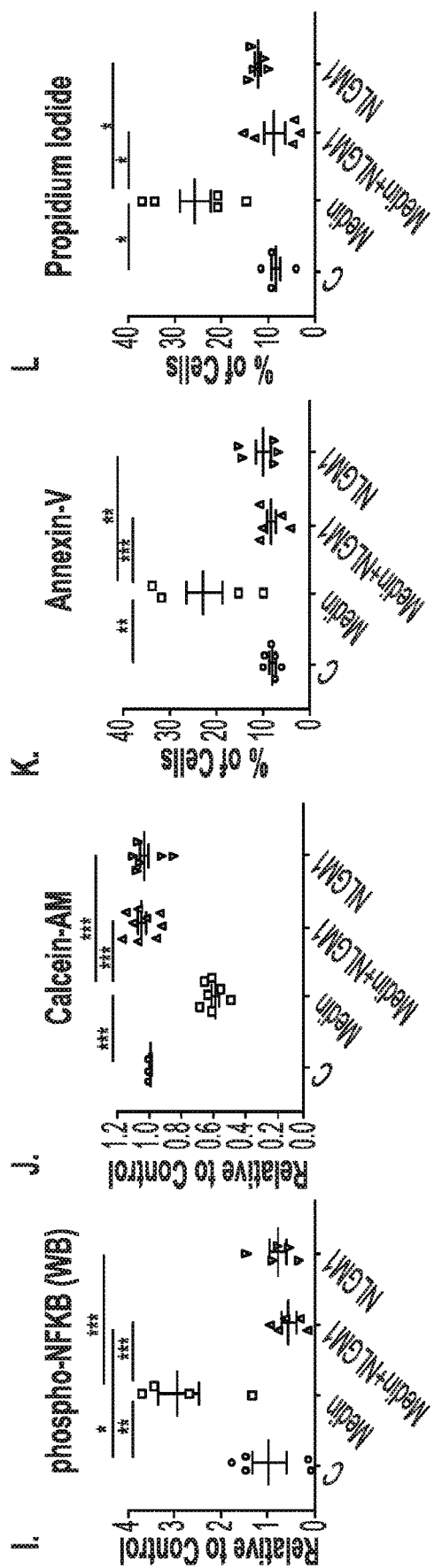

NLGM1 protects against immune activation and cytotoxicity of medin. NLGM1 co-treatment with medin resulted in abolition of medin-induced increases in EC IL-8, IL-6, ICAM-1 and PAI-1 production (FIG. 7A-H). It also prevented NFκB activation by medin (FIG. 7I). Unlike the findings with co-treatment with specific NFκB inhibitor, NLGM1 co-treatment prevented medin cytotoxicity (FIG. 7J-L).

Figures 8A, 8B:
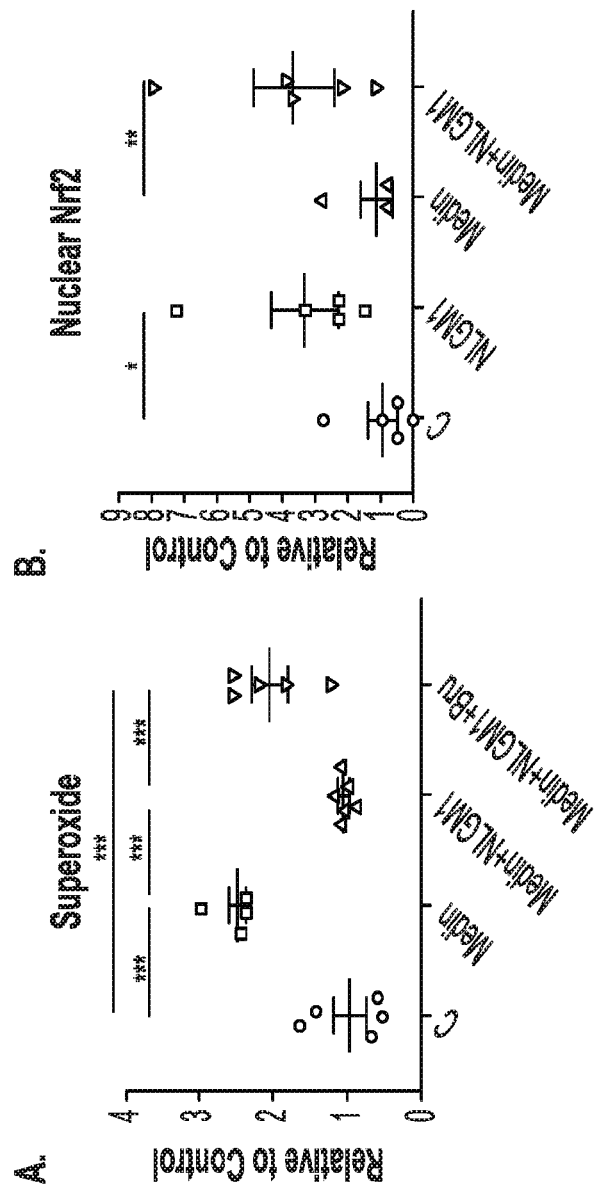
FIGS. 8A-K show NLGM1 protection against medin cytotoxicity is Nrf2-dependent.
Figures 8C, 8D:
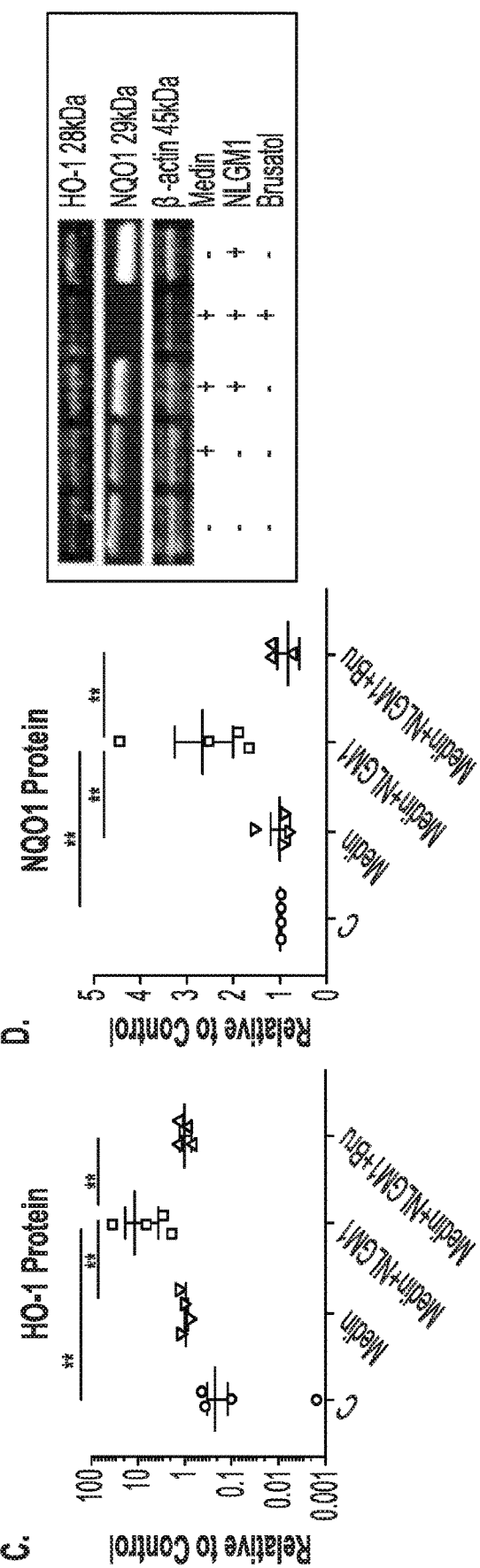

To evaluate the mechanism behind NLGM1 protection against medin, EC oxidative stress was assessed by measuring production of superoxide by flow cytometry (dihydroethidium fluorescence). Medin increased EC superoxide production that was reversed by co-treatment with NLGM1 (FIG. 8A). This protective effect was abolished when co-treated with brusatol, a specific inhibitor of Nrf2[32]. Nrf2 controls the expression of an array of antioxidant response element-dependent genes and regulates antioxidant defense[33], including expression of HO-1 and NQO1. ECs treated with NLGM1 showed increase in nuclear Nrf2 and co-treatment of medin with NLGM1 increased nuclear Nrf2, HO-1 and NQO1 protein expression compared to medin treatment alone (FIG. 8B-D). Addition of brusatol abolished the increase in HO-1 and NQO1 (FIG. 8B-D).

Figure 8E:
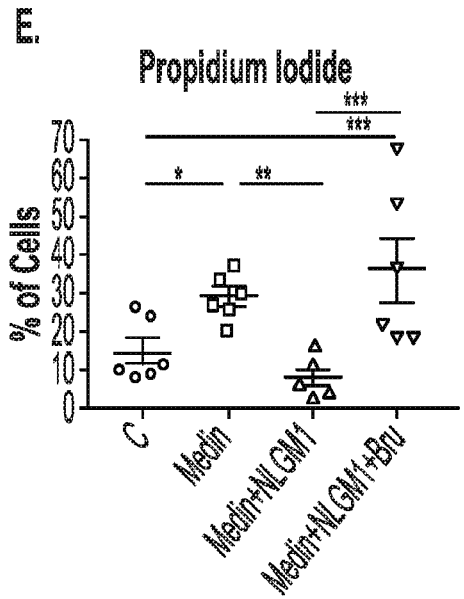
Figure 8F:
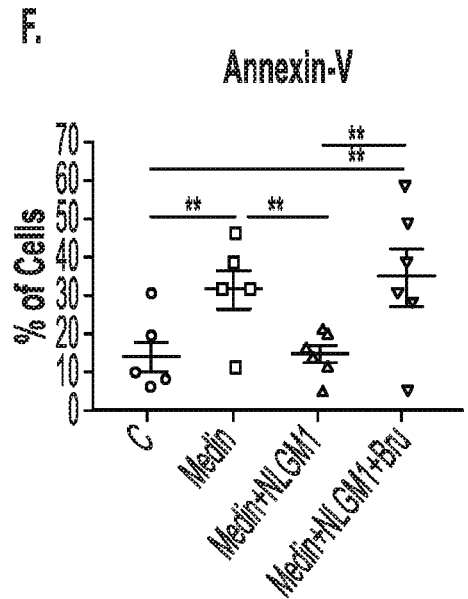
Figure 8G:
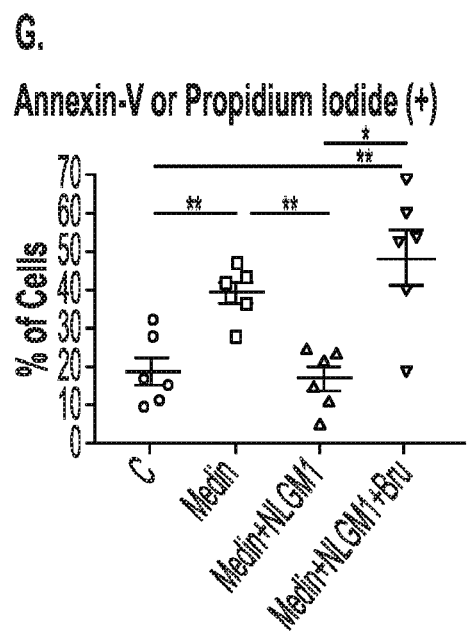
Figure 8I:
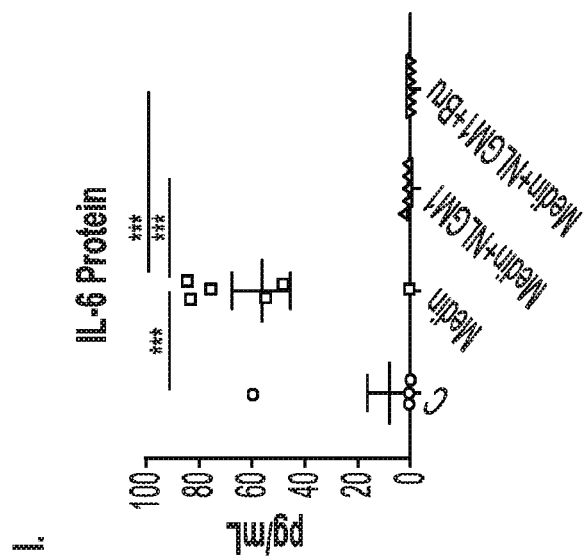
Figure 8H:
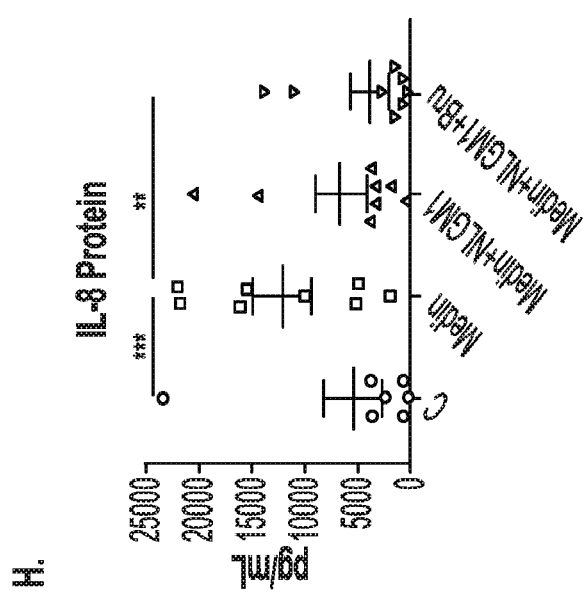
Figure 8K:
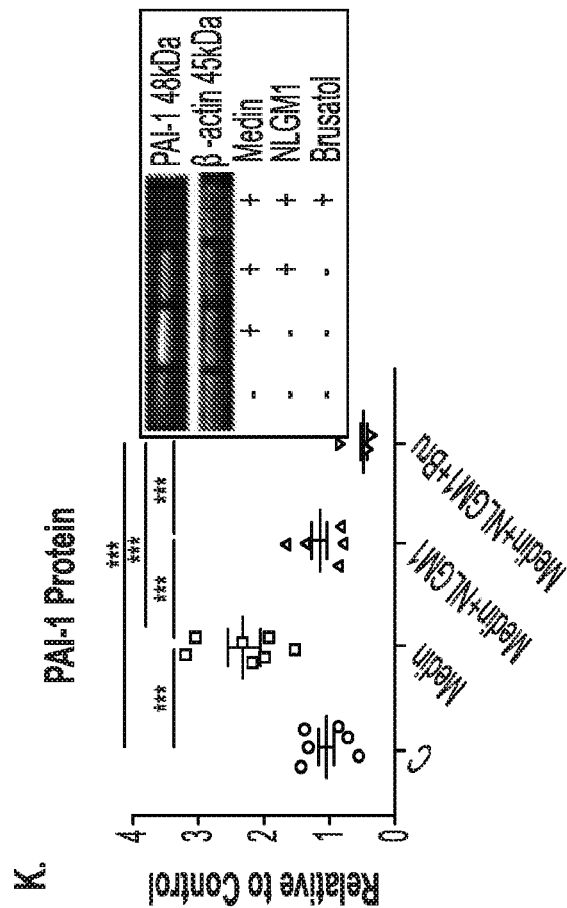
Figure 8J:
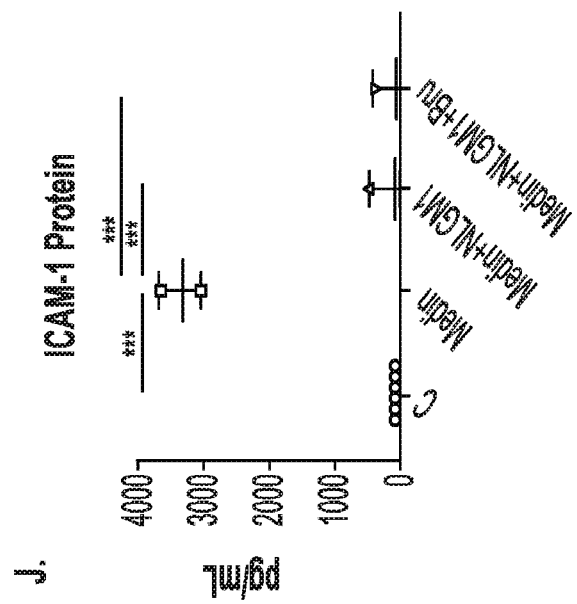

To assess whether NLGM1 cytoprotection against medin is Nrf2-dependent, ECs were treated with medin alone, medin plus NLGM1 without or with brusatol. Results show that the protective effect of NLGM1 in terms of cell viability is reversed by brusatol (FIG. 8E-G). To assess whether NLGM1 attenuation of medin-induced immune activation is Nrf-2 dependent, same treatments were performed, and immune activation markers were measured. Unlike viability assays, co-treatment with brusatol did not reverse NLGM1 protective effect against medin-induced increases in IL-8, IL-6, ICAM-1 and PAI-1 (FIG. 8H-K).

Endothelial cells modulate astrocyte activation following medin treatment. To evaluate whether medin-induced immune activation of ECs affects astrocyte inflammatory response, monocultures of human astrocytes were exposed to vehicle control, medin (5 μM), conditioned media from ECs treated with vehicle, or conditioned media from ECs treated with medin (5 μM). Results showed significant increase in astrocyte IL-8 production when astrocytes were exposed to medin-treated EC media. Following this, a custom-built 3D cell co-culture chip was developed where the outer channels are infusible and seeded with ECs, and the inner channel seeded with collagen-encapsulated astrocytes with 100 μm gaps allowing diffusion of agents from the outer EC layer to the inner astrocyte layer. A computer simulation with COMSOL Multiphysics software was used to administer 5 μM medin through the side channels in media at 37° C. and diffuse through the collagen hydrogel within the inner chamber. This demonstrates the extent of diffusion through the hydrogel 5 minutes and at 20 hours after administration, there is complete diffusion through the hydrogel resulting in uniform concentration throughout as predicted computationally. Experimentally, following seeding of the chip, astrocyte processes were seen to extend towards other astrocytes as well towards endothelial cells. Vehicle or medin was infused for 20 hours in outer channels in chips with or without seeded ECs. Astrocyte media IL-8 was shown to be significantly higher in medin treated chips with ECs when compared to medin treated chips without ECs showing modulation of astrocyte response by ECs exposed to medin.

Discussion. The study demonstrates the following findings. First, cerebral arterioles from elderly human brain donors contain medin, and arteriole medin is higher in VaD compared to CN participants. Cerebral arteriole medin was also higher in donors with higher cerebral white matter lesion scores. Secondly, medin induced human EC cytotoxicity and NFκB-mediated immune activation with increased proinflammatory and prothrombotic cytokines (IL-8, IL-6, ICAM-1 and PAI-1). Thirdly, the results show that the inflammatory astrocyte response was enhanced when exposed to medin-treated endothelial cells or their conditioned media. Collectively, these findings suggest that medin may serve as a risk factor and treatment target for cerebrovascular inflammation that could modulate neuroinflammation. Lastly, the results demonstrate that NLGM1, by inhibiting NFκB activation and promoting Nrf2-dependent antioxidant responses, can reverse medin's adverse effects.

Despite being one of the most common human amyloid proteins[4, 5], little is known about the physiologic/pathologic effects of medin. Based on limited available data, medin has been proposed as a potential biologic agent influencing vascular aging[34] because of its aging-related deposition in blood vessels[6, 7]. The association between medin and aortic wall degeneration[8] and possible link with arterial inflammation[9]. Aortic medin deposition is well-documented, but there is lack of data, on the prevalence of medin accumulation in cerebral vessels and its potential pathophysiologic role in CVD. The results described herein show that cerebral arteriole medin is commonly found in elderly individuals, with higher levels seen in VaD compared to CN donors. A potential pathologic contribution or association is supported by the observation that cerebral arteriole medin is increased in donors with higher CWML scores. CWML are commonly seen in VaD and aging brains, are believed to be due to ischemic microvascular injury and their presence is associated with triple the risk of stroke and double the risk of dementia[14, 21]. The pathologic role of medin is further supported mechanistically by previous findings that show that medin causes endothelial dysfunction in human cerebral arterioles[6] and the current findings showing a more extensive immune activation effect of medin on ECs with increased ICAM-1, PAI-1, IL-8 and IL-6. ICAM-1 is a transmembrane protein that facilitates leukocyte adhesion and endothelial transmigration[35]; it also has pro-inflammatory signal transduction effects that promote leukocyte and macrophage recruitment[36]. ICAM-1 is elevated in subarachnoid hemorrhage[37] and ischemic stroke[38], biologic nidus for later development of VaD[39]. PAI-1 inhibits tissue plasminogen activator and urokinase which are plasminogen activators; by doing so, PAI-1 inhibits plasmin-mediated fibrinolysis, and is pro-thrombotic[40]. Consistent with the results disclosed herein, PAI-1 expression was shown by others to be increased by NFκB-mediated inflammatory stimuli[41]. Elevated PAI-1 was reported in VaD patients, and hemostasis abnormalities were more frequent and marked in VaD as compared to Alzheimer's disease[42]. IL-8 and IL-6 function as leukocyte chemoattractants[43]. Plasma IL-6 was noted to be independently associated with functional impairment in older individuals with VaD but not Alzheimer's disease[44]. Levels of IL-8 correlated with severity of cognitive impairment in VaD[45]. The finding that medin causes EC immune activation when placed in the context of the observation that cerebral arteriole medin is increased in VaD and in donors with higher CWML scores suggests a role for medin in VaD pathophysiology.

Established mechanisms linking small vessel CVD and VaD include hypoxic/ischemic injury from vessel occlusion/ flow limiting obstruction, vascular microbleeds, and lipohyalinosis; the latter involves the interplay of vascular inflammation and reactive gliosis of astrocytes, microglia and oligodendrocytes leading to connective tissue hyaline deposition that disrupts blood brain barrier integrity[46]. Histopathologic analysis showed that CWMLs were associated with both endothelial and glial activation[13]. The findings disclosed herein show increased GFAP-expressing astrocytes in VaD brains with the observation that more astrocytes are closer (within 100 μm) to a cerebral arteriole than farther away. The astrocyte monoculture and chip EC-astrocyte co-culture data show that IL-8 production is enhanced when astrocytes are exposed to medin-treated ECs. These in-vitro and brain histology results support a modulating role of medin-induced EC immune activation in enhancing neuroinflammation. Neuroinflammatory mechanisms are suspected to play an important role in VaD[45, 47]. Since inflammatory cytokine-mediated interactions between glia cells and neurons could contribute to cognitive impairment[12, 15, 48], it is reasonable to speculate that medin might also modulate cognitive function through vascular inflammatory mechanisms.

Medin-mediated EC immune activation is dependent on NFκB activation, an important primary transcription factor regulating cellular immune response[49], as shown by the reversal by RO106-9920, a selective inhibitor of IκBα degradation and NFκB activation[27]. NLGM1 also inhibited NFκB activation, leading to reversal of medin-induced increases in IL-8, IL-6, ICAM-1 and PAI-1. However, NFκB inhibition by RO1-169920 did not restore EC viability following exposure to medin, suggesting distinct signaling mechanisms between immune activation and cellular viability. NLGM1, unlike RO1-169920, fully restored EC viability.

It was previously shown that NLGM1 induced activation of Nrf2 (manifested by nuclear translocation from cytosol), a transcription factor that regulates expression of antioxidant proteins to protect against oxidative damage[33], leading to protection of ECs against light chain amyloid injury[16]. Similar to effects observed with light chain amyloid protein, medin increased EC superoxide production. Despite inducing oxidative stress, no accompanying Nrf2 activation was elicited by medin, nor change in antioxidant HO-1 and NQO1 expression. NLGM1 cotreatment prevented increased superoxide production; it increased nuclear Nrf2 and protein expression of HO-1 and NQO1, two Nrf2-dependent antioxidant enzymes[50, 51]. The cytoprotective effect of NLGM1 against medin is confirmed to be Nrf2-dependent because co-treatment with brusatol, a specific inhibitor of Nrf2[32], reversed the protective effect of NLGM1 on superoxide production and EC cell viability while preventing increases in antioxidant enzymes HO-1 and HQO1. Interestingly, Nrf2 inhibition did not prevent NLGM1 from reversing medin-induced EC immune activation, again suggesting distinct signaling mechanisms. The findings that NLGM1 restored EC viability and prevented immune activation by medin point to an agent and therapeutic approach against medin-induced vasculopathy. It was previously showed that NLGM1 can also protect against amyloid light chain-induced oxidative stress by the same mechanism[33]. Structural and pathological[52, 53] similarities between amyloid proteins are well-established.

Conclusions. The biologic effects of medin, one of the most common human amyloid proteins is unknown. Described herein is the prevalence of cerebral arteriole medin in elderly brain donors with higher values in vascular dementia as compared to cognitively normal patients, and increased arteriole medin in donors with higher CWML scores. Medin impaired endothelial cell viability and induced profound endothelial immune activation that modulated astrocyte activation. The findings point to a role of medin in vascular inflammation which in turn could modulate neuroinflammation, making it a target to elucidate the pathophysiology of aging-related CVD and vascular dementia. NLGM1, via effects on NFκB and Nrf2 signaling, reverses medin's adverse effects and represents a needed therapeutic approach.

REFERENCES

1. Yoshitake T, Kiyohara Y, Kato I, Ohmura T, Iwamoto H, Nakayama K, Ohmori S, Nomiyama K, Kawano H, Ueda K and et al. Incidence and risk factors of vascular dementia and Alzheimer's disease in a defined elderly Japanese population: the Hisayama Study. *Neurology.* 1995; 45:1161-8.
2. Ungvari Z, Buffenstein R, Austad S N, Podlutsky A, Kaley G and Csiszar A. Oxidative stress in vascular senescence: lessons from successfully aging species. *Front Biosci.* 2008; 13:5056-70.
3. Ungvari Z, Kaley G, de Cabo R, Sonntag W E and Csiszar A. Mechanisms of vascular aging: new perspectives. *J Gerontol A Biol Sci Med Sci.* 2010; 65:1028-41.
4. Haggqvist B, Naslund J, Sletten K, Westermark G T, Mucchiano G, Tjernberg L O, Nordstedt C, Engstrom U and Westermark P. Medin: an integral fragment of aortic smooth muscle cell-produced lactadherin forms the most common human amyloid. *Proceedings of the National Academy of Sciences of the United States of America.* 1999; 96:8669-74.
5. Larsson A, Soderberg L, Westermark G T, Sletten K, Engstrom U, Tjernberg L O, Naslund J and Westermark P. Unwinding fibril formation of medin, the peptide of the most common form of human amyloid. *Biochem Biophys Res Commun.* 2007; 361:822-8.
6. Migrino R Q, Davies H A, Truran S, Karamanova N, Franco D A, Beach T G, Serrano G E, Truong D, Nikkhah M and Madine J. Amyloidogenic medin induces endothelial dysfunction and vascular inflammation through the receptor for advanced glycation endproducts. *Cardiovasc Res.* 2017; 113:1389-1402.
7. Peng S, Glennert J and Westermark P. Medin-amyloid: a recently characterized age-associated arterial amyloid form affects mainly arteries in the upper part of the body. *Amyloid: the international journal of experimental and clinical investigation: the official journal of the International Society of Amyloidosis.* 2005; 12:96-102.
8. Peng S, Larsson A, Wassberg E, Gerwins P, Thelin S, Fu X and Westermark P. Role of aggregated medin in the pathogenesis of thoracic aortic aneurysm and dissection. *Laboratory investigation; a journal of technical methods and pathology.* 2007; 87:1195-205.
9. Peng S, Westermark G T, Naslund J, Haggqvist B, Glennert J and Westermark P. Medin and medin-amyloid in ageing inflamed and non-inflamed temporal arteries. *The Journal of pathology.* 2002; 196:91-6.
10. Migrino R Q, Truran S, Karamanova N, Serrano G E, Madrigal C, Davies H A, Madine J, Reaven P and Beach T G. Human cerebral collateral arteriole function in subjects with normal cognition, mild cognitive impairment, and dementia. *Am J Physiol Heart Circ Physiol.* 2018; 315:H284-H290.
11. Simpson J E, Fernando M S, Clark L, Ince P G, Matthews F, Forster G, O'Brien J T, Barber R, Kalaria R N, Brayne C, Shaw P J, Lewis C E, Wharton S B, Function MRCC and Ageing Neuropathology Study G. White matter lesions in an unselected cohort of the elderly: astrocytic, microglial and oligodendrocyte precursor cell responses. *Neuropathol Appl Neurobiol.* 2007; 33:410-9.
12. Rosenberg G A. Inflammation and white matter damage in vascular cognitive impairment. *Stroke; a journal of cerebral circulation.* 2009; 40:520-3.
13. Fernando M S, O'Brien J T, Perry R H, English P, Forster G, McMeekin W, Slade J Y, Golkhar A, Matthews F E, Barber R, Kalaria R N, Ince P G and Neuropathology Group of MC. Comparison of the pathology of cerebral white matter with post-mortem magnetic resonance imaging (MRI) in the elderly brain. *Neuropathol Appl Neurobiol.* 2004; 30:385-95.
14. Wardlaw J M, Valdes Hernandez M D C and Munoz Maniega S. What are white matter hyperintensities made of? Relevance to vascular cognitive impairment. *J Am Heart Assoc.* 2015.
15. Heppner F L, Ransohoff R M and Becher B. Immune attack: the role of inflammation in Alzheimer disease. *Nature reviews Neuroscience.* 2015; 16:358-72.
16. Franco D A, Truran S, Weissig V, Guzman-Villanueva D, Karamanova N, Senapati S, Burciu C, Ramirez-Alvarado M, Blancas-Mejia L M, Lindsay S, Hari P and Migrino R Q. Monosialoganglioside-Containing Nanoliposomes Restore Endothelial Function Impaired by AL Amyloidosis Light Chain Proteins. *J Am Heart Assoc.* 2016; 5.
17. Truran S, Weissig V, Madine J, Davies H A, Guzman-Villanueva D, Karamanova N, Serrano G, Beach T G and Migrino R Q. Nanoliposomes protect against human arteriole endothelial dysfunction induced by B-amyloid peptide. *J Cereb Blood Flow Metab.* 2015; 36:405-12.
18. Beach T G, Adler C H, Sue L I, Serrano G, Shill H A, Walker D G, Lue L, Roher A E, Dugger B N, Maarouf C, Birdsill A C, Intorcia A, Saxon-Labelle M, Pullen J, Scroggins A, Filon J, Scott S, Hoffman B, Garcia A, Caviness J N, Hentz J G, Driver-Dunckley E, Jacobson S A, Davis K J, Belden C M, Long K E, Malek-Ahmadi M, Powell J J, Gale L D, Nicholson L R, Caselli R J, Woodruff B K, Rapscak S Z, Ahern G L, Shi J, Burke A D, Reiman E M and Sabbagh M N. Arizona Study of Aging and Neurodegenerative Disorders and Brain and Body Donation Program. *Neuropathology.* 2015; 35:354-89.
19. Roman G C, Tatemichi T K, Erkinjuntti T, Cummings J L, Masdeu J C, Garcia J H, Amaducci L, Orgogozo J M, Brun A, Hofman A and et al. Vascular dementia: diagnostic criteria for research studies. Report of the NINDS-AIREN International Workshop. *Neurology.* 1993; 43:250-60.
20. Davies H A, Wilkinson M C, Gibson R P and Middleton D A. Expression and purification of the aortic amyloid polypeptide medin. *Protein Expr Purif* 2014; 98:32-7.
21. Prins N D and Scheltens P. White matter hyperintensities, cognitive impairment and dementia: an update. *Nat Rev Neurol.* 2015; 11:157-65.
22. Choi S A, Evidente V G, Caviness J N, Shill H A, Sabbagh M N, Connor D J, Hentz J G, Adler C H and Beach T G. Are there differences in cerebral white matter lesion burdens between Parkinson's disease patients with or without dementia? *Acta Neuropathol.* 2010; 119:147-9.
23. Kitazume S, Tachida Y, Kato M, Yamaguchi Y, Honda T, Hashimoto Y, Wada Y, Saito T, Iwata N, Saido T and Taniguchi N. Brain endothelial cells produce amyloid {beta} from amyloid precursor protein 770 and preferentially secrete the O-glycosylated form. *J Biol Chem.* 2010; 285:40097-103.
24. Ma J F, Wang H M, Li Q Y, Zhang Y, Pan J, Qiang Q, Xin X Y, Tang H D, Ding J Q and Chen S D. Starvation triggers Abeta42 generation from human umbilical vascular endothelial cells. *FEBS Lett.* 2010; 584:3101-6.
25. Chao A C, Lee T C, Juo S H and Yang D I. Hyperglycemia Increases the Production of Amyloid Beta-Peptide Leading to Decreased Endothelial Tight Junction. *CNS Neurosci Ther.* 2016; 22:291-7.
26. Gomez-Gaviro M V, Scott C E, Sesay A K, Matheu A, Booth S, Galichet C and Lovell-Badge R. Betacellulin promotes cell proliferation in the neural stem cell niche and stimulates neurogenesis. *Proceedings of the National Academy of Sciences of the United States of America.* 2012; 109:1317-22.
27. Swinney D C, Xu Y Z, Scarafia L E, Lee I, Mak A Y, Gan Q F, Ramesha C S, Mulkins M A, Dunn J, So O Y, Biegel T, Dinh M, Volkel P, Barnett J, Dalrymple S A, Lee S and Huber M. A small molecule ubiquitination inhibitor blocks NF-kappa B-dependent cytokine expression in cells and rats. *J Biol Chem.* 2002; 277:23573-81.
28. Bindokas V P, Jordan J, Lee C C and Miller R J. Superoxide production in rat hippocampal neurons: selective imaging with hydroethidine. *J Neurosci.* 1996; 16:1324-36.
29. Neri S, Mariani E, Meneghetti A, Cattini L and Facchini A. Calcein-acetyoxymethyl cytotoxicity assay: standardization of a method allowing additional analyses on recovered effector cells and supernatants. *Clin Diagn Lab Immunol.* 2001; 8:1131-5.
30. Migrino R Q, Truran S, Gutterman D D, Franco D A, Bright M, Schlundt B, Timmons M, Motta A, Phillips S A and Hari P. Human microvascular dysfunction and apoptotic injury induced by AL amyloidosis light chain proteins. *Am J Physiol Heart Circ Physiol.* 2011; 301:H2305-12.
31. Brahmachari S, Fung Y K and Pahan K. Induction of glial fibrillary acidic protein expression in astrocytes by nitric oxide. *J Neurosci.* 2006; 26:4930-9.
32. Olayanju A, Copple I M, Bryan H K, Edge G T, Sison R L, Wong M W, Lai Z Q, Lin Z X, Dunn K, Sanderson C M, Alghanem A F, Cross M J, Ellis E C, Ingelman-Sundberg M, Malik H Z, Kitteringham N R, Goldring C E and Park B K. Brusatol provokes a rapid and transient inhibition of Nrf2 signaling and sensitizes mammalian cells to chemical toxicity-implications for therapeutic targeting of Nrf2. *Free Radic Biol Med.* 2015; 78:202-12.
33. Ma Q. Role of nrf2 in oxidative stress and toxicity. *Annu Rev Pharmacol Toxicol.* 2013; 53:401-26.
34. Lakatta E G. The reality of aging viewed from the arterial wall. *Artery research.* 2013; 7:73-80.
35. Yang L, Froio R M, Sciuto T E, Dvorak A M, Alon R and Luscinskas F W. ICAM-1 regulates neutrophil adhesion and transcellular migration of TNF-alpha-activated vascular endothelium under flow. *Blood.* 2005; 106:584-92.
36. Etienne-Manneville S, Chaverot N, Strosberg A D and Couraud P O. ICAM-1-coupled signaling pathways in astrocytes converge to cyclic AMP response element-binding protein phosphorylation and TNF-alpha secretion. *J Immunol.* 1999; 163:668-74.
37. Polin R S, Bavbek M, Shaffrey M E, Billups K, Bogaev C A, Kassell N F and Lee K S. Detection of soluble E-selectin, ICAM-1, VCAM-1, and L-selectin in the cerebrospinal fluid of patients after subarachnoid hemorrhage. *J Neurosurg.* 1998; 89:559-67.

38. Frijns C J and Kappelle L J. Inflammatory cell adhesion molecules in ischemic cerebrovascular disease. *Stroke; a journal of cerebral circulation.* 2002; 33:2115-22.

39. Corraini P, Henderson V W, Ording A G, Pedersen L, Horvath-Puho E and Sorensen H T. Long-Term Risk of Dementia Among Survivors of Ischemic or Hemorrhagic Stroke. *Stroke; a journal of cerebral circulation.* 2017; 48:180-186.

40. Vaughan D E. PAI-1 and atherothrombosis. *J Thromb Haemost.* 2005; 3:1879-83.

41. Kruithof E K. Regulation of plasminogen activator inhibitor type 1 gene expression by inflammatory mediators and statins. *Thromb Haemost.* 2008; 100:969-75.

42. Mari D, Parnetti L, Coppola R, Bottasso B, Reboldi G P, Senin U and Mannucci P M. Hemostasis abnormalities in patients with vascular dementia and Alzheimer's disease. *Thromb Haemost.* 1996; 75:216-8.

43. Mantovani A, Bussolino F and Dejana E. Cytokine regulation of endothelial cell function. *FASEB journal: official publication of the Federation of American Societies for Experimental Biology.* 1992; 6:2591-9.

44. Zuliani G, Guerra G, Ranzini M, Rossi L, Munari M R, Zurlo A, Ble A, Volpato S, Atti A R and Fellin R. High interleukin-6 plasma levels are associated with functional impairment in older patients with vascular dementia. *Int J Geriatr Psychiatry.* 2007; 22:305-11.

45. Schmitz M, Hermann P, Oikonomou P, Stoeck K, Ebert E, Poliakova T, Schmidt C, Llorens F, Zafar S and Zerr I. Cytokine profiles and the role of cellular prion protein in patients with vascular dementia and vascular encephalopathy. *Neurobiol Aging.* 2015; 36:2597-606.

46. Shabir O, Berwick J and Francis S E. Neurovascular dysfunction in vascular dementia, Alzheimer's and atherosclerosis. *BMC Neurosci.* 2018; 19:62.

47. Iadecola C. The overlap between neurodegenerative and vascular factors in the pathogenesis of dementia. *Acta Neuropathol.* 2010; 120:287-96.

48. Rubio-Perez J M and Morillas-Ruiz J M. A review: inflammatory process in Alzheimer's disease, role of cytokines. *ScientificWorldJournal.* 2012; 2012:756357.

49. Gilmore T D. Introduction to NF-kappaB: players, pathways, perspectives. *Oncogene.* 2006; 25:6680-4.

50. Araujo J A, Zhang M and Yin F. Heme oxygenase-1, oxidation, inflammation, and atherosclerosis. *Front Pharmacol.* 2012; 3:119.

51. Dinkova-Kostova A T and Talalay P. NAD(P)H:quinone acceptor oxidoreductase 1 (NQO1), a multifunctional antioxidant enzyme and exceptionally versatile cytoprotector. *Arch Biochem Biophys.* 2010; 501:116-23.

52. Schubert D, Behl C, Lesley R, Brack A, Dargusch R, Sagara Y and Kimura H. Amyloid peptides are toxic via a common oxidative mechanism. *Proceedings of the National Academy of Sciences of the United States of America.* 1995; 92:1989-93.

53. Pastor M T, Kummerer N, Schubert V, Esteras-Chopo A, Dotti C G, Lopez de la Paz M and Serrano L. Amyloid toxicity is independent of polypeptide sequence, length and chirality. *Journal of molecular biology.* 2008; 375: 695-707.

What is claimed is:

1. A method of ameliorating one or more symptoms of medin-mediated cerebrovascular disease, the method comprising administering to a subject with the medin-mediated cerebrovascular disease, wherein the medin-mediated cerebrovascular disease is vascular dementia, stroke, Biswanger's disease, transient ischemic attack, cerebral infarction, or occlusion or stenosis of cerebral arteries, a composition comprising a nanoliposome and GM1 in an amount effective to ameliorate one more symptoms of medin-mediated cerebrovascular disease in the subject, wherein the nanoliposome comprises a phospholipid and cholesterol, wherein the phospholipid, the cholesterol, and the GM1 are present in a molar ratio of 70:25:5, respectively, thereby ameliorating one or more symptoms of the medin-mediated cerebrovascular disease.

2. The method of claim 1, wherein the phospholipid is phosphatidylcholine.

3. The method of claim 1, wherein the nanoliposome is less than 50 nm.

* * * * *